US012734123B2

(12) United States Patent
Lechner et al.

(10) Patent No.: US 12,734,123 B2
(45) **Date of Patent: *Sep. 15, 2026**

(54) METHOD FOR DYEING KERATINOUS MATERIAL, COMPRISING THE USE OF AN ORGANOSILICON COMPOUND, A COLORED EFFECT PIGMENT AND A FILM-FORMING POLYMER IV

(71) Applicant: Henkel AG & Co. KGaA, Duesseldorf (DE)

(72) Inventors: Torsten Lechner, Langenfeld (DE); Gabriele Weser, Neuss (DE); Claudia Kolonko, Remscheid (DE); Caroline Kriener, Duesseldorf (DE); Ulrike Schumacher, Duesseldorf (DE); Marc Nowottny, Monchengladbach (DE); Juergen Schoepgens, Schwalmtal (DE); Phillip Jaiser, Langenfeld (DE); Carsten Mathiaszyk, Essen (DE); Jing Hodes, Hagen (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 1204 days.

This patent is subject to a terminal disclaimer.

(21) Appl. No.: 17/628,134

(22) PCT Filed: Jul. 6, 2020

(86) PCT No.: PCT/EP2020/068959

§ 371 (c)(1),
(2) Date: Jan. 18, 2022

(87) PCT Pub. No.: WO2021/013511

PCT Pub. Date: Jan. 28, 2021

(65) Prior Publication Data

US 2022/0257490 A1 Aug. 18, 2022

(30) Foreign Application Priority Data

Jul. 19, 2019 (DE) ........................ 102019210691.9

(51) Int. Cl.
*A61K 8/58* (2006.01)
*A61K 8/02* (2006.01)
*A61K 8/26* (2006.01)
*A61Q 5/06* (2006.01)

(52) U.S. Cl.
CPC ............ *A61K 8/585* (2013.01); *A61K 8/0258* (2013.01); *A61K 8/26* (2013.01); *A61Q 5/065* (2013.01); *A61K 2800/436* (2013.01); *A61K 2800/61* (2013.01)

(58) Field of Classification Search
CPC ......... A61K 8/0258; A61Q 5/065; A61Q 5/10
See application file for complete search history.

(56) References Cited

U.S. PATENT DOCUMENTS

| | | | | |
|---|---|---|---|---|
| 7,806,941 B2 * | 10/2010 | Brun | A61Q 5/10 | 8/405 |
| 2006/0110351 A1 * | 5/2006 | Koehler | A61Q 5/04 | 8/406 |
| 2010/0083446 A1 * | 4/2010 | Brun | A61K 8/891 | 8/405 |
| 2018/0140519 A1 * | 5/2018 | Bazin De Bezons | A61Q 1/06 | |

FOREIGN PATENT DOCUMENTS

| | | | |
|---|---|---|---|
| CN | 104244913 | A | 12/2014 |
| EP | 2168633 | A2 | 3/2010 |
| FR | 3031672 | A1 | 7/2016 |
| JP | 2017514823 | A | 6/2017 |
| WO | 2013160363 | A2 | 10/2013 |
| WO | 2015166454 | A1 | 11/2015 |
| WO | 2020035359 | A1 | 2/2020 |

* cited by examiner

*Primary Examiner* — Mark V Stevens
(74) *Attorney, Agent, or Firm* — Ingrassia Fisher & Lorenz, LLP

(57) ABSTRACT

A process for dyeing keratinous material, in particular human hair, is provided. The process includes applying an agent (a) to the keratinous material, the agent (a) including at least one organic silicon compound. An agent (b) is applied to the keratinous material. The agent (b) includes (b1) at least one coloring compound including at least one effect pigment including i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal particle carrier layer, and (b2) at least one film-forming polymer.

19 Claims, No Drawings

METHOD FOR DYEING KERATINOUS MATERIAL, COMPRISING THE USE OF AN ORGANOSILICON COMPOUND, A COLORED EFFECT PIGMENT AND A FILM-FORMING POLYMER IV

CROSS-REFERENCE TO RELATED APPLICATION

This application is a U.S. National-Stage entry under 35 U.S.C. § 371 based on International Application No. PCT/EP2020/068959, filed Jul. 6, 2020, which was published under PCT Article 21(2) and which claims priority to German Application No. 102019210691.9, filed Jul. 19, 2019, which are all hereby incorporated in their entirety by reference.

TECHNICAL FIELD

The subject of the present application is a process for dyeing keratinous material, in particular human hair, which comprises the application of two different agents (a), and (b). The agent (a) comprises at least one organic silicon compound. The agent (b) comprises at least one coloring compound (b2) comprising at least one selected effect pigment.

The second subject-matter of this application is a multi-component packaging unit (kit-of-parts) for coloring keratinous material, in particular human hair, which comprises the agents (a) and (b) separately packaged in two different containers.

BACKGROUND

Changing the shape and color of keratinous material, especially human hair, is a key area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between 5 and 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed again without residue by a few washes with detergents comprising surfactants. Various products of this type are available on the market under the name hair mascara.

If the user desires a particularly long-lasting coloring of his hair, the use of oxidative dyes is his only option so far. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes.

EP 2168633 B1 deals with the task of producing long-lasting hair colorations using pigments. The paper teaches that when a combination of pigment, organic silicon compound, hydrophobic polymer and a solvent is used on hair, it is possible to create colorations that are said to be particularly resistant to shampooing.

Metallic luster pigments or metallic effect pigments are widely used in many fields of technology. They are used, for example, to color coatings, printing inks, inks, plastics, glasses, ceramic products and preparations for decorative cosmetics such as nail polish. They are exemplified by their attractive angle-dependent color impression (goniochromism) and their metallic-looking luster.

BRIEF SUMMARY

Processes for dyeing keratinous material, in particular human hair, are provided. In an exemplary embodiment, the process includes applying an agent (a) to the keratinous material. The agent (a) includes (a1) at least one organic silicon compound. The process further includes applying an agent (b) to the keratinous material. The agent (b) includes (b1) at least one coloring compound including at least one effect pigment including i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal particle carrier layer, and (b2) at least one film-forming polymer.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Hair with a metallic finish or metallic highlights are in trend. The metallic tone makes the hair look thicker and shinier.

There is a need to provide hair dyes with effect pigments that on the one hand have high wash and rub fastness and on the other hand do not negatively affect hair properties such as manageability and feel. For this purpose, it would be desirable if the effect pigments used had a high covering power and could be applied to the hair in thin layers.

Accordingly, the task of the present disclosure was to provide a coloring system with effect pigments that has fastness properties comparable to oxidative coloring. Wash fastness properties should be outstanding, but the use of oxidation dye precursors normally used for this purpose should be avoided.

Surprisingly, it has now been found that the task can be excellently solved if keratinous materials, in particular human hair, are colored by a process in which at least two agents (a) and (b) are applied to the keratinous materials (hair). Here, the agent (a) comprises at least one organic silicon compound, and the agent (b) comprises at least one selected effect pigment (b1) and a film-forming polymer (b2).

When the two agents (a) and (b) were used in a dyeing process, keratinous material could be dyed with particularly high color intensity and high fastness properties.

A first object of the present disclosure is a method for coloring keratinous material, in particular human hair, comprising the following steps:

application of an agent (a) to the keratinous material, the agent (a) comprising at least one organic silicon compound, and Application of an agent (b) to the keratinous material, wherein the agent (b) comprises:

(b1) at least one coloring compound comprising at least one effect pigment comprising i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal particle carrier layer, and (b2) at least one film-forming polymer.

In the effect pigments, interference colors with high chroma are developed by interference between the light reflected from the surface of the substrate platelet and the light reflected from the surfaces of the metal particles.

Accordingly, with the help of the "colored" effect pigments, keratin fibers can be dyed in particularly intensive and numerous color shades.

Keratinous Material

Keratinous material includes hair, skin, nails (such as fingernails and/or toenails). Wool, furs and feathers also fall under the definition of keratinous material.

Preferably, keratinous material is understood to be human hair, human skin and human nails, especially fingernails and toenails. Keratinous material is understood to be human hair.

Agent (a) and (b)

In the process, agents (a) and (b) are applied to the keratinous material, in particular human hair. The two agents (a) and (b) are different from each other.

Accordingly, a method for dyeing keratinous material, in particular human hair, is disclosed, comprising the following steps:

application of an agent (a) to the keratinous material, the agent (a) comprising at least one organic silicon compound, and Application of an agent (b) to the keratinous material, wherein the agent (b) comprises:

(b1) at least one coloring compound comprising at least one effect pigment comprising i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal particle carrier layer, and (b2) and at least one film-forming polymer, where the two agents (a) and (b) are different from each other.

Agent (a)

Agent (a) is exemplified by its content of at least one organic silicon compound, in particular at least one organic silane. The organic silicon compounds or organic silanes included in agent (a) is reactive compounds.

Agent (a) comprises the organic silicon compound(s), in particular the organic silane(s), in a cosmetic carrier which may be hydrated, low in water or anhydrous. In addition, the cosmetic carrier can be liquid, gel-like, creamy, pasty, powdery or even solid (e.g., in the form of a tablet or a pressed product). Preferably, the cosmetic carrier of the agent (a) is an aqueous or aqueous-alcoholic carrier. For hair coloring, such carriers are, for example, creams, emulsions, gels or also surfactant-comprising foaming solutions, such as shampoos, foam aerosols, foam formulations or other preparations suitable for application to the hair.

The cosmetic carrier preferably comprises water, which means that the carrier comprises at least 2% by weight of water based on its weight. Preferably, the water content is above 5 wt. %, further preferably above 10 wt. % still further preferably above 15 wt. %. The cosmetic carrier can also be aqueous-alcoholic. Aqueous/alcoholic solutions in the context of the present disclosure are aqueous solutions comprising 2 to 70% by weight of a $C_1$-$C_4$ alcohol, more particularly ethanol or isopropanol. The agents may additionally contain other organic solvents, such as methoxybutanol, benzyl alcohol, ethyl diglycol or 1,2-propylene glycol. Preferred are all water-soluble organic solvents.

The term "coloring agent" is used in the context of the present disclosure to refer to a coloring of keratinous material, in particular human hair, brought about using pigments and/or direct dyes. During this coloring process, the coloring compounds are deposited in a particularly homogeneous and smooth film on the surface of the keratinous material or diffuse into the keratinous fiber. The film is formed in situ by oligomerization or polymerization of the organic silicon compound(s), and by the interaction of organic silicon compound with the colorant compounds.

Organic Silicon Compounds

As an essential component of the present disclosure, the agent (a) comprises at least one organic silicon compound (a1). Preferred organic silicon compounds (a1) are selected from silanes having one, two or three silicon atoms.

Organic silicon compounds, alternatively called organosilicon compounds, are compounds which either have a direct silicon-carbon bond (Si—C) or in which the carbon is bonded to the silicon atom via an oxygen, nitrogen or sulfur atom. The organic silicon compounds are preferably compounds comprising one to three silicon atoms. Organic silicon compounds preferably contain one or two silicon atoms.

The agent (a) particularly preferably comprises at least one organic silicon compound (a1) selected from silanes having one, two or three silicon atoms.

According to IUPAC rules, the term silane chemical compounds based on a silicon skeleton and hydrogen. In organic silanes, the hydrogen atoms are completely or partially replaced by organic groups such as (substituted) alkyl groups and/or alkoxy groups. In organic silanes, some of the hydrogen atoms may also be replaced by hydroxy groups.

In a particularly preferred embodiment, the method is exemplified by the application of an agent (a) to the keratinous material, wherein the agent (a) comprises at least one organic silicon compound selected from silanes having one, two or three silicon atoms.

The agent (a) particularly preferably comprises at least one organic silicon compound selected from silanes having one, two or three silicon atoms, the organic silicon compound further comprising one or more basic chemical functions and one or more hydroxyl groups or hydrolyzable groups per molecule.

In a particularly preferred embodiment, the method is exemplified by the application of an agent (a) to the keratinous material, said agent (a) comprising at least one organic silicon compound (a1) selected from silanes having one, two or three silicon atoms, said organic silicon compound further comprising one or more basic chemical functions and one or more hydroxyl groups or hydrolyzable groups per molecule.

This basic group can be, for example, an amino group, an alkylamino group, a dialkylamino group or a trialkylamino group, which is preferably connected to a silicon atom via a linker. Preferably, the basic group is an amino group, a $C_1$-$C_6$ alkylamino group or a Di($C_1$-$C_6$)alkylamino group.

The hydrolyzable group(s) is (are) preferably a $C_1$-$C_6$ alkoxy group, especially an ethoxy group or a methoxy group. It is preferred when the hydrolyzable group is directly bonded to the silicon atom. For example, if the hydrolyzable group is an ethoxy group, the organic silicon compound preferably comprises a structural unit R'R"R'"Si—O—$CH_2$—$CH_3$. The radicals R', R" and R'" represent the three remaining free valences of the silicon atom.

A very particularly preferred method is wherein the agent (a) comprises at least one organic silicon compound selected from silanes having one, two or three silicon atoms, the organic silicon compound preferably comprising one or more basic chemical functions and one or more hydroxyl groups or hydrolyzable groups per molecule.

Particularly satisfactory results were obtained when the agent (a) comprises at least one organic silicon (a1) compound of formula (I) and/or (II).

In another very particularly preferred embodiment, a method is wherein an agent (a) is applied to the keratinous material or human hair, wherein the agent (a) comprises at least one organic silicon compound (a1) of formula (I) and/or (II),

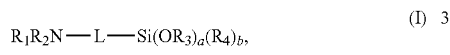

(I)

where $R_1$, $R_2$ independently represent a hydrogen atom or a $C_1$-$C_6$ alkyl group, L is a linear or branched bivalent $C_1$-$C_{20}$ alkylene group, $R_3$ is a hydrogen atom or a $C_1$-$C_6$ alkyl group, $R_4$ represents a $C_1$-$C_6$ alkyl group a, represents an integer from 1 to 3, and b stands for the integer 3-a,

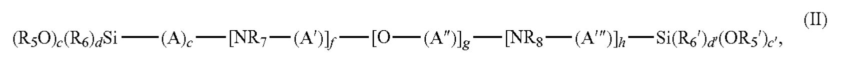

(II)

where

R5, R5', R5" independently represent a hydrogen atom or a $C_1$-$C_6$ alkyl group, R6, R6' and R6" independently represent a $C_1$-$C_6$ alkyl group, A, A', A", A'" and A"" independently represent a linear or divalent, bivalent $C_1$-$C_{20}$ alkylene group, $R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III)

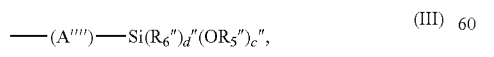

(III)

c, stands for an integer from 1 to 3, d stands for the integer 3-c, c' stands for an integer from 1 to 3, d' stands for the integer 3-c', c" stands for an integer from 1 to 3, d" stands for the integer 3-c", e stands for 0 or 1, f stands for 0 or 1, g stands for 0 or 1, h stands for 0 or 1, provided that at least one of e, f, g and h is different from 0.

The substituents $R_1$, $R_2$, $R_3$, $R_4$, $R_5$, $R_5$', $R_5$", $R_6$, $R_6$', $R_6$", $R_7$, $R_8$, L, A, A', A", A'" and A"" in the compounds of formula (I) and (II) are explained below as examples: Examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl radicals. Examples of a $C_2$-$C_6$ alkenyl group are vinyl, allyl, but-2-enyl, but-3-enyl and isobutenyl, preferred $C_2$-$C_6$ alkenyl radicals are vinyl and allyl. Preferred examples of a hydroxy $C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino $C_1$-$C_6$ alkyl group are the aminomethyl group, the 2-aminoethyl group, the 3-aminopropyl group. The 2-aminoethyl group is particularly preferred. Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In the organic silicon compounds (a1) of the formula (I)

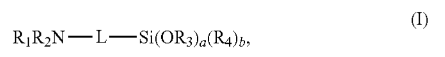

(I)

the radicals $R_1$ and $R_2$ independently of one another represent a hydrogen atom or a $C_1$-$C_6$ alkyl group. Very preferably, $R_1$ and $R_2$ both represent a hydrogen atom.

In the middle part of the organic silicon compound (a1) is the structural unit or the linker -L- which stands for a linear or divalent, bivalent $C_1$-$C_{20}$ alkylene group.

Preferably -L- stands for a linear, bivalent $C_1$-$C_{20}$ alkylene group. Further preferably -L- stands for a linear bivalent $C_1$-$C_6$ alkylene group. Particularly preferred -L stands for a methylene group ($CH_2$—), an ethylene group (—$CH_2$—$CH_2$—), propylene group (—$CH_2$—$CH_2$—$CH_2$—) or butylene (—$CH_2$—$CH_2$—$CH_2$—$CH_2$—). L stands for a propylene group (—$CH_2$—$CH_2$—$CH_2$—)

The organic silicon compounds (a1) of the formula (I)

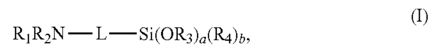

(I)

one end of each carries the silicon-comprising group —Si$(OR_3)_a(R_4)_b$.

In the terminal structural unit $—Si(OR_3)_a(R_4)_b$, $R_3$ is hydrogen or $C_1$-$C_6$ alkyl group, and $R_4$ is $C_1$-$C_6$ alkyl group. R3 and $R_4$ independently of each other represent a methyl group or an ethyl group.

Here a stands for an integer from 1 to 3, and b stands for the integer 3-a. If a stands for the number 3, then b is equal to 0. If a stands for the number 2, then b is equal to 1. If a stands for the number 1, then b is equal to 2.

Dyeing's with the best wash fastnesses could be obtained if the agent (a) comprises at least one organic silicon compound (a1) of formula (I) in which the radicals $R_3$, $R_4$ independently of one another represent a methyl group or an ethyl group.

Furthermore, dyeing's with the best wash fastnesses could be obtained if the agent (a) comprises at least one organic silicon compound (a1) corresponding to formula (I): in which the radical a is the number 3. In this case the rest b stands for the number 0.

In another preferred embodiment, an agent (a) is wherein it comprises at least one organic silicon compound (a1) of the formula (I), where $R_3$, $R_4$ independently of one another represent a methyl group or an ethyl group and a stands for the number 3 and b stands for the number 0.

In a further preferred embodiment, the method is wherein the agent (a) comprises at least one organic silicon compound (a1) of formula (I),

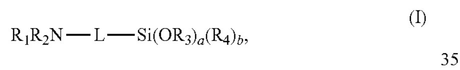

(I)

where $R_1$, $R_2$ both represent a hydrogen atom, and

L represents a linear, bivalent $C_1$-$C_6$-alkylene group, preferably a propylene group ($—CH_2—CH_2—CH_2—$) or an ethylene group ($—CH_2—CH_2—$), $R_3$ represents a hydrogen atom, an ethyl group or a methyl group, $R_4$ represents a methyl group or an ethyl group, a stands for the number 3 and b stands for the number 0.

When b is 0, the radical $R_4$ does not occur in the compounds of formula (I).

Accordingly, in a further preferred embodiment, the method is wherein the agent (a) comprises at least one organic silicon compound (a1) of formula (I),

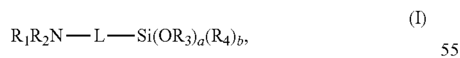

(I)

where $R_1$, $R_2$ both represent a hydrogen atom, and

L represents a linear, bivalent $C_1$-$C_6$-alkylene group, preferably a propylene group ($—CH_2—CH_2—CH_2—$) or an ethylene group ($—CH_2—CH_2—$), $R_3$ represents a hydrogen atom, an ethyl group or a methyl group, a stands for the number 3 and b stands for the number 0.

Organic silicon compounds (a1) of the formula (I) which are particularly suitable for solving the problem are

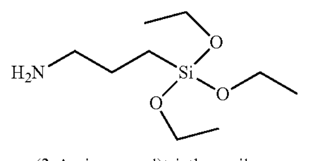

(3-Aminopropyl)triethoxysilane

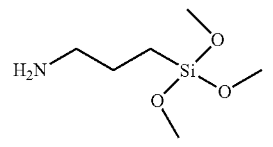

(3-Aminopropyl)trimethoxysilane

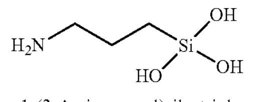

1-(3-Aminopropyl)silantriol

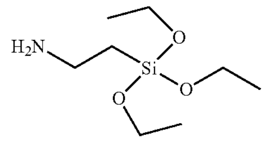

(2-Aminoethyl)triethoxysilane

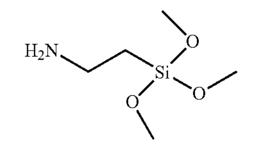

(2-Aminoethyl)trimethoxysilane

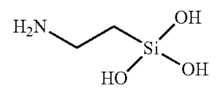

1-(2-Aminoethyl)silantriol

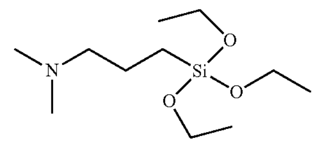

(3-Dimethylaminopropyl)triethoxysilane

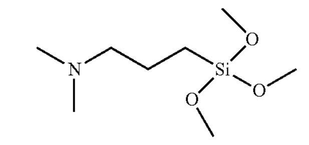

(3-Dimethylaminopropyl)trimethoxysilane

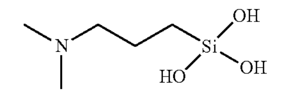

1-(3-Dimethylaminopropyl)silantriol

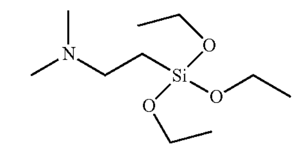

(2-Dimethylaminoethyl)triethoxysilane

-continued

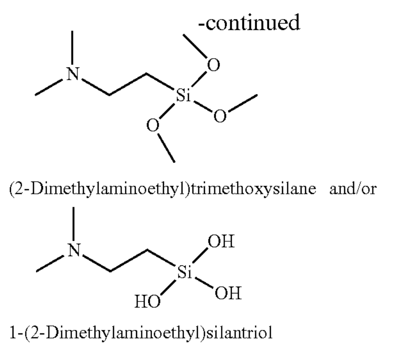

(2-Dimethylaminoethyl)trimethoxysilane and/or 1-(2-Dimethylaminoethyl)silantriol to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is 1. If c' stands for the number 1, then d' is 2.

Dyeing's with the best wash fastness values could be obtained if the residues c and c' both stand for the number 3. In this case d and d' both stand for the number 0.

In a further preferred embodiment, the method is wherein the agent (a) comprises at least one organic silicon compound (a1) of formula (II),

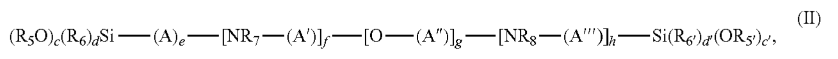

$$(R_5O)_c(R_6)_dSi—(A)_e—[NR_7—(A')]_f—[O—(A'')]_g—[NR_8—(A''')]_h—Si(R_{6'})_{d'}(OR_{5'})_{c'}, \quad (II)$$

In another preferred embodiment, the method is wherein the agent (a) comprises at least one organic silicon compound (a1) of formula (I) selected from the group of (3-Aminopropyl)triethoxysilane
(3-Aminopropyl)trimethoxysilane
1-(3-Aminopropyl)silantriol
(2-Aminoethyl)triethoxysilane
(2-Aminoethyl)trimethoxysilane
1-(2-Aminoethyl)silantriol
(3-Dimethylaminopropyl)triethoxysilane
(3-Dimethylaminopropyl)trimethoxysilane
1-(3-Dimethylaminopropyl)silantriol
(2-Dimethylaminoethyl)triethoxysilane.
(2-Dimethylaminoethyl)trimethoxysilane,
1-(2-Dimethylaminoethyl)silantriol and mixtures thereof.

The above mentioned organic silicon compound (a1) of formula (I) is commercially available.

(3-aminopropyl)trimethoxysilane, for example, can be purchased from Sigma-Aldrich. (3-aminopropyl)triethoxysilane is also commercially available from Sigma-Aldrich.

In a further embodiment, the agent (a) comprises at least one organic silicon compound of formula (II)

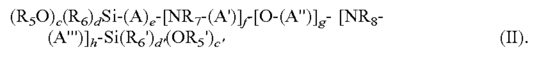

$$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II).$$

The organosilicon compounds (a1) of the formula (II) each carry at their two ends the silicon-comprising groupings $(R_5O)_c(R_6)_dSi—$ und $—Si(R_6')_{d'}(OR_5')_{c'}$.

In the central part of the molecule of formula (II) there are the groups $-(A)_e-$ and $—[NR_7-(A')]_f-$ and $—[O-(A'')]_g-$ and $—[NR_8-(A''')]_h-$. Here, each of the radicals e, f, g and h can independently of one another stand for the number 0 or 1, with the proviso that at least one of the radicals e, f, g and h is different from 0. In other words, an organic silicon compound of formula (II) comprises at least one grouping selected from the group of -(A)- and $—[NR_7-(A')]-$ and —[O-(A'')]- and $—[NR_8-(A''')]-$.

In the two terminal structural units $(R_5O)_c(R_6)_dSi—$ and $—Si(R_6')_{d'}(OR_5')_c$, the radicals R5, R5', R5'' independently of one another represent a hydrogen atom or a $C_1$-$C_6$ alkyl group. The radicals R6, R6' and R6'' independently represent a $C_1$-$C_6$ alkyl group.

Here c stands for an integer from 1 to 3, and d stands for the integer 3-c. If c stands for the number 3, then d is equal where R5 and R5' independently represent a methyl group or an ethyl group, c and c' both stand for the number 3 and d and d' both stand for the number 0.

When c and c' both represent the number 3 and d and d' both represent the number 0, the organic silicon compounds correspond to formula (IIa)

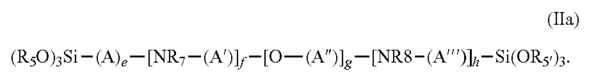

$$(R_5O)_3Si-(A)_e-[NR_7-(A')]_f-[O-(A'')]_g-[NR8-(A''')]_h-Si(OR_{5'})_3. \quad (IIa)$$

The radicals e, f, g and h can independently stand for the number 0 or 1, whereby at least one radical from e, f, g and h is different from zero. The abbreviations e, f, g and h thus define which of the groupings $-(A)_e-$ and $—[NR_7-(A')]_f-$ and $—[O-(A'')]_g-$ and $—[NR_8-(A''')]_h-$ are in the middle part of the organic silicon compound of formula (II).

In this context, the presence of certain groupings has proved to be particularly beneficial in terms of increasing washability. Particularly satisfactory results were obtained when at least two of the residues e, f, g and h stand for the number 1. Especially preferred e and f both stand for the number 1. Furthermore, g and h both stand for the number 0.

When e and f are both 1 and g and h are both 0, the organic silicon compound (a1) is represented by the formula (IIb)

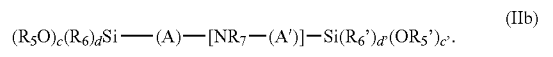

$$(R_5O)_c(R_6)_dSi—(A)—[NR_7—(A')]-Si(R_6')_{d'}(OR_5')_{c'}. \quad (IIb)$$

The radicals A, A', A'', A''' and A'''' independently represent a linear or divalent, bivalent $C_1$-$C_{20}$ alkylene group. Preferably the radicals A, A', A'', A''' and A'''' independently of one another represent a linear, bivalent $C_1$-$C_{20}$ alkylene group. Further preferably the radicals A, A', A'', A''' and A'''' independently represent a linear bivalent $C_1$-$C_6$ alkylene group. In particular, the radicals A, A', A'', A''' and A'''' independently of one another represent a methylene group ($—CH_2—$), an ethylene group ($—CH_2—CH_2—$), a propylene group ($—CH_2—CH_2—CH_2—$) or a butylene group ($—CH_2—CH_2—CH_2—CH_2—$). Very preferably, the radicals A, A', A'', A''' and A'''' represent a propylene group ($—CH_2—CH_2—CH_2—$).

If the radical f represents the number 1, then the organic silicon compound of formula (II) comprises a structural grouping —$[NR_7\text{-}(A')]$-.

If the radical h represents the number 1, then the organic silicon compound of formula (II) comprises a structural grouping —$[NR_8\text{-}(A''')]$-.

Wherein $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (III)

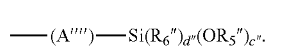

(III)

Very preferably, $R_7$ and $R_8$ independently represent a hydrogen atom, a methyl group, a 2-hydroxyethyl group, a 2-alkenyl group, a 2-aminoethyl group or a grouping of formula (III).

If the radical f represents the number 1 and the radical h represents the number 0, the organic silicon compound comprises the grouping $[NR_7\text{-}(A')]$ but not the grouping —$[NR_8\text{-}(A''')]$. If the radical R7 now stands for a grouping of the formula (III), the agent (a) comprises an organic silicon compound with 3 reactive silane groups.

In a further preferred embodiment, the method is wherein the agent (a) comprises at least one organic silicon compound (a1) of formula (II),

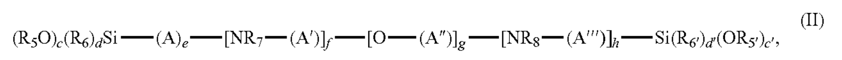

(II)

where e and f both stand for the number 1, g and h both stand for the number 0,

A and A' independently represent a linear, bivalent $C_1$-$C_6$ alkylene group, and R7 represents a hydrogen atom, a methyl group, a 2-hydroxyethyl group, a 2-alkenyl group, a 2-aminoethyl group or a group of formula (III).

In a further preferred embodiment, the method is wherein the agent (a) comprises at least one organic silicon compound (a1) of formula (II), wherein e and f both stand for the number 1, g and h both stand for the number 0, A and A' independently of one another represent a methylene group ($—CH_2—$), an ethylene group ($—CH_2—CH_2—$) or a propylene group ($—CH_2—CH_2—CH_2$), and R7 represents a hydrogen atom, a methyl group, a 2-hydroxyethyl group, a 2-alkenyl group, a 2-aminoethyl group or a group of formula (III).

Organic silicon compounds (a1) of the formula (II) that are well suited for solving the problem are

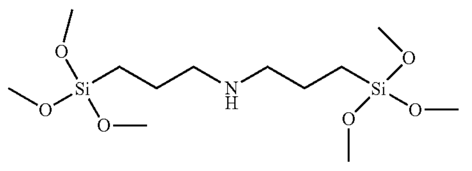

3-(Trimethoxysilyl)-N-[3-(trimethoxysilyl)propyl]-1-propanamine

-continued

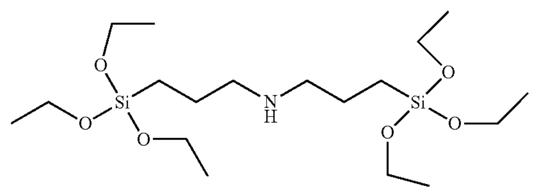

3-(Triethoxysilyl)-N-[3-(triethoxysilyl)propyl]-1-propanamine

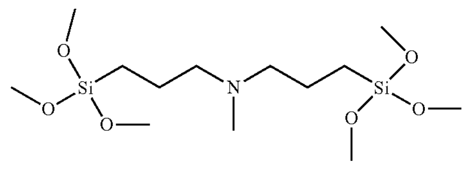

N-Methyl-3-(trimethoxysilyl)-N-[3-(trimethoxysilyl)propyl]-1-propanamine

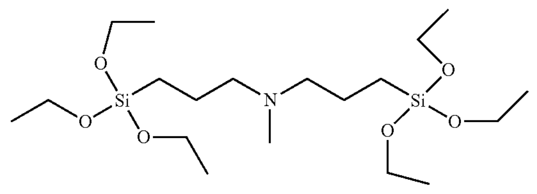

N-Methyl-3-(triethoxysilyl)-N-[3-(triethoxysilyl)propyl]-1-propanamine

-continued

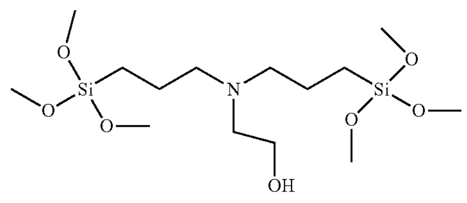

2-[Bis[3-(trimethoxysilyl)propyl]amino]-ethanol

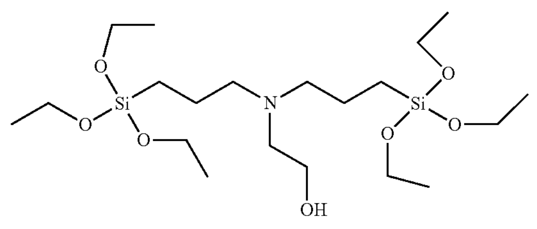

2-[Bis[3-(triethoxysilyl)propyl]amino]ethanol

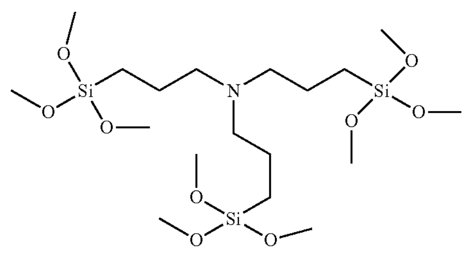

3-(Trimethoxysilyl)-N,N-bis[3-(trimethoxysilyl)propyl]-1-propanamine

-continued

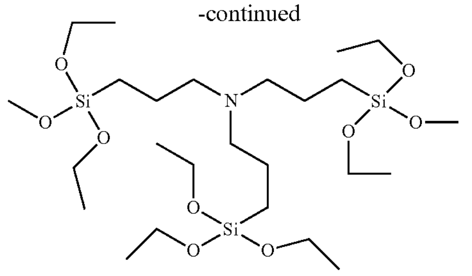

3-(Triethoxysilyl)-N,N-bis[3-(triethoxysilyl) propyl]-1-propanamine

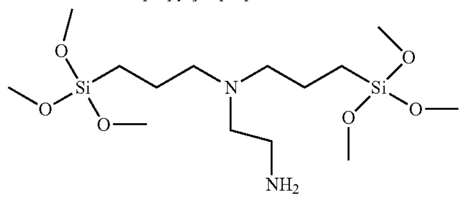

N1,N1-Bis[3-(trimethoxysilyl)propyl]-1,2-ethanediamine ,

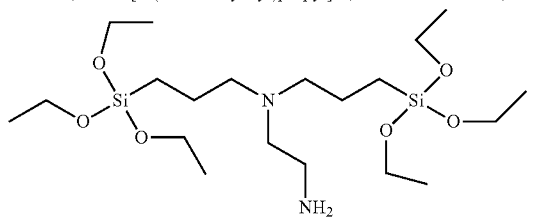

N1,N1-Bis[3-(triethoxysilyl)propyl]-1,2-ethanediamine ,

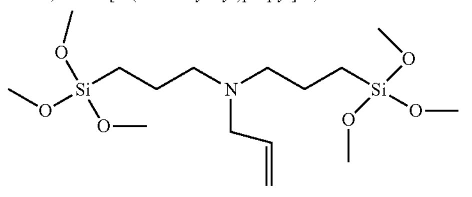

N,N-Bis[3-(trimethoxysilyl)propyl]-2-propene-1-amine

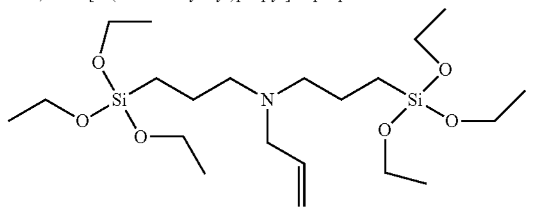

N,N-Bis[3-(triethoxysilyl)propyl]-2-propene-1-amine

The above mentioned organic silicon compound (a1) of formula (II) is commercially available.

Bis(trimethoxysilylpropyl)amines with the CAS number 82985-35-1 can be purchased from Sigma-Aldrich.

Bis[3-(triethoxysilyl)propyl]amines with the CAS number 13497-18-2 can be purchased from Sigma-Aldrich, for example.

N-methyl-3-(trimethoxysilyl)-N-[3-(trimethoxysilyl)propyl]-1-propanamine is alternatively referred to as Bis(3-trimethoxysilylpropyl)-N-methylamine and can be purchased commercially from Sigma-Aldrich or Fluorochem.

3-(triethoxysilyl)-N,N-bis[3-(triethoxysilyl)propyl]-1-propanamine with the CAS number 18784-74-2 can be purchased for example from Fluorochem or Sigma-Aldrich.

In another preferred embodiment, an agent (a) is wherein it comprises at least one organic silicon compound (a1) of formula (II) selected from the group of 3-(Trimethoxysilyl)-N-[3-(trimethoxysilyl)propyl]-1-propanamine
3-(Triethoxysilyl)-N-[3-(triethoxysilyl) propyl]-1-propanamine
N-Methyl-3-(trimethoxysilyl)-N-[3-(trimethoxysilyl)propyl]-1-propanamine
N-Methyl-3-(triethoxysilyl)-N-[3-(triethoxysilyl) propyl]-1-propanamine
2-[Bis[3-(trimethoxysilyl) propyl]amino]-ethanol
2-[Bis[3-(triethoxysilyl) propyl]amino]ethanol
3-(Trimethoxysilyl)-N,N-bis[3-(trimethoxysilyl) propyl]-1-propanamine
3-(Triethoxysilyl)-N,N-bis[3-(triethoxysilyl) propyl]-1-propanamine
N1,N1-Bis[3-(trimethoxysilyl) propyl]-1,2-ethanediamine,
N1,N1-Bis[3-(triethoxysilyl) propyl]-1,2-ethanediamine,
N,N-Bis[3-(trimethoxysilyl)propyl]-2-Propen-1-amine and/or
N,N-Bis[3-(triethoxysilyl)propyl]-2-propen-1-amine.

In further dyeing tests, it has also been found to be particularly advantageous if the agent (a) applied to the keratinous material in the process comprises at least one organic silicon compound (a1) of the formula (IV)

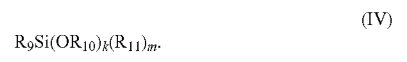

$$R_9Si(OR_{10})_k(R_{11})_m. \quad (IV)$$

The organic silicon compound(s) (a1) of formula (IV) may also be referred to as silanes of the alkylalkoxysilane or alkylhydroxysilane type,

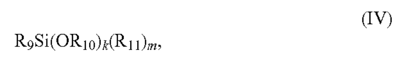

$$R_9Si(OR_{10})_k(R_{11})_m, \quad (IV)$$

where $R_9$ stands for a $C_1$-$C_{18}$ alkyl group, $R_{10}$ represents a hydrogen atom or a $C_1$-$C_6$ alkyl group, $R_{11}$ represents a $C_1$-$C_6$ alkyl group k is an integer from 1 to 3, and m stands for the integer 3-k.

In a further preferred embodiment, the method is wherein the agent (a) comprises at least one organic silicon compound (a1) of formula (IV).

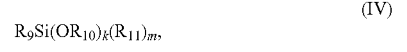

$$R_9Si(OR_{10})_k(R_{11})_m, \quad (IV)$$

where $R_9$ stands for a $C_1$-$C_{18}$ alkyl group, $R_{10}$ represents a hydrogen atom or a $C_1$-$C_6$ alkyl group, $R_{11}$ represents a $C_1$-$C_6$ alkyl group k is an integer from 1 to 3, and m stands for the integer 3-k.

In a further preferred embodiment, the method is wherein the agent (a) comprises, in addition to the organic silicon compound or compounds (a1) of the formula (I), at least one further organic silicon compound (a1) of the formula (IV)

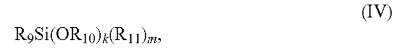

$$R_9Si(OR_{10})_k(R_{11})_m, \quad (IV)$$

where $R_9$ stands for a $C_1$-$C_{18}$ alkyl group, $R_{10}$ represents a hydrogen atom or a $C_1$-$C_6$ alkyl group, $R_{11}$ represents a $C_1$-$C_6$ alkyl group k is an integer from 1 to 3, and m stands for the integer 3-k.

In a further preferred embodiment, the method is wherein the agent (a) comprises, in addition to the organic silicon compound or compounds (a1) of the formula (II), at least one further organic silicon compound (a1) of the formula (IV)

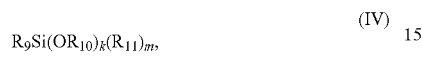

(IV)

where $R_9$ stands for a $C_1$-$C_{18}$ alkyl group, $R_{10}$ represents a hydrogen atom or a $C_1$-$C_6$ alkyl group, $R_{11}$ represents a $C_1$-$C_6$ alkyl group k is an integer from 1 to 3, and m stands for the integer 3-k.

In a further preferred embodiment, the method is wherein the agent (a) comprises, in addition to the organic silicon compound or compounds (a1) of the formula (I) and/or (II), at least one further organic silicon compound (a1) of the formula (IV)

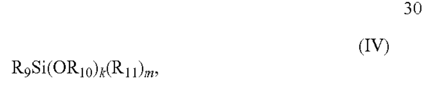

(IV)

where $R_9$ stands for a $C_1$-$C_{18}$ alkyl group, $R_{10}$ represents a hydrogen atom or a $C_1$-$C_6$ alkyl group, $R_{11}$ represents a $C_1$-$C_6$ alkyl group k is an integer from 1 to 3, and m stands for the integer 3-k.

In the organic silicon compounds (a1) of formula (IV), the $R_9$ radical is a $C_1$-$C_{18}$ alkyl group. This $C_1$-$C_{18}$ alkyl group is saturated and can be linear or branched. Preferably, $R_9$ represents a linear $C_1$-$C_{18}$ alkyl group. Preferably, $R_9$ represents a methyl group, an ethyl group, an n-propyl group, an n-butyl group, an n-pentyl group, an n-hexyl group, an n-octyl group, an n-dodecyl group or an n-octadecyl group. Particularly preferably, $R_9$ represents a methyl group, an ethyl group, an n-propyl group, an n-hexyl group or an n-octyl group.

In the organic silicon compounds (a1) of formula (IV), the radical $R_{10}$ represents a hydrogen atom or a $C_1$-$C_6$ alkyl group. Highly preferred $R_{10}$ stands for a methyl group or an ethyl group.

In the organic silicon compounds (a1) of formula (IV), the radical $R_{11}$ represents a $C_1$-$C_6$ alkyl group. R11 stands for a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Dyeing's with the best wash fastnesses were obtained when an agent (a) comprising at least one organic silicon compound (a1) corresponding to formula (IV): in which the radical k is the number 3, was used in the process. In this case the rest m stands for the number 0.

Organic silicon compounds (a1) of the formula (IV) which are particularly suitable for solving the problem as contemplated herein are

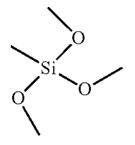

Methyltrimethoxysilane

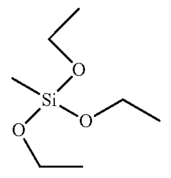

Methyltriethoxysilane

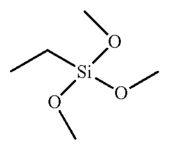

Ethyltrimethoxysilane

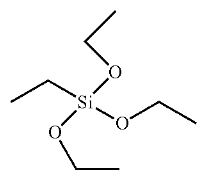

Ethyltriethoxysilane

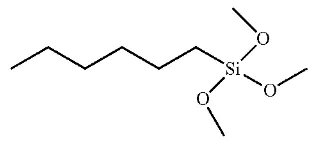

n-Hexyltrimethoxysilane

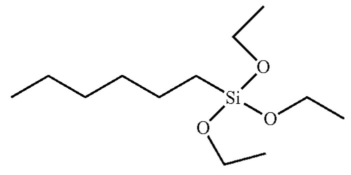

n-Hexyltriethoxysilane

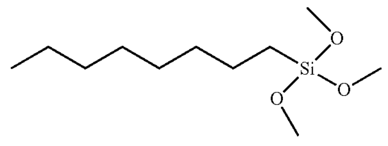

n-Octyltrimethoxysilane

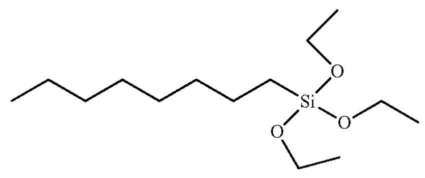

n-Octyltriethoxysilane

-continued

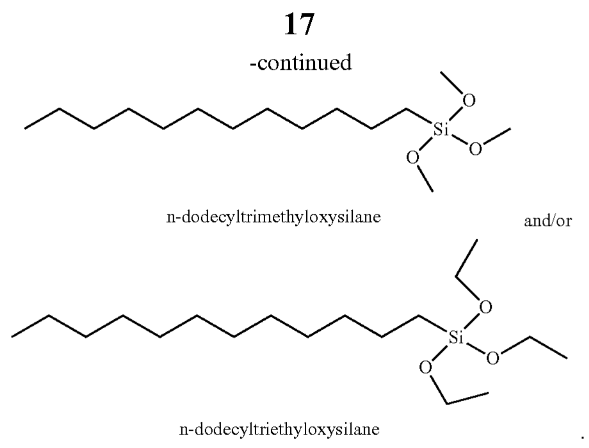

n-dodecyltrimethyloxysilane and/or n-dodecyltriethyloxysilane.

n-octadecyltrimethoxysilane and/or n-octadecyltriethoxysilane.

In another preferred embodiment, the method is wherein the agent (a) comprises at least one organic silicon compound (a1) of formula (IV) selected from the group of Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane
Dodecyltriethoxysilane.
Octadecyltrimethoxysilane and/or
Octadecyltriethoxysilane.

In the course of the work leading to this present disclosure, it was found that particularly stable and uniform films could be obtained on the keratinous material even when the agent (a) included two organic silicon compounds that were structurally different from each other.

In another preferred embodiment, a method is wherein the agent (a) comprises at least two structurally different organic silicon compounds.

In a preferred embodiment, a process is wherein an agent (a) comprising at least one organic silicon compound of formula (I) and at least one organic silicon compound of formula (IV) is applied to the keratinous material.

In an explicitly quite particularly preferred embodiment, the process is wherein an agent (a) is applied to the keratinous material, which agent (a1) comprises at least one organic silicon compound of the formula (I) selected from the group of (3-aminopropyl)triethoxysilane and (3-aminopropyl)trimethoxysilane and additionally comprises at least one organic silicon compound of formula (IV) selected from the group of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

The organic silicon compounds described above are reactive compounds. In this context, it has been found preferable if the agent (a)—based on the total weight of the agent (a)—comprises one or more organic silicon compounds (a1) in a total amount of 0.1 to 20% by weight, preferably 0.5 to 15% by weight and particularly preferably 5.0 to 10% by weight.

In this context, it has been found to be particularly preferred if the agent (a) comprises—based on the total weight of the agent (a)—one or more organic silicon compounds (a1) of the formula (I) and/or (II) in a total amount of 0.1 to 20% by weight, preferably 0.2 to 15% by weight and particularly preferably 0.2 to 3% by weight.

It has further been found to be particularly preferred if the agent (a) comprises—based on the total weight of the agent (a)—one or more organic silicon compounds (a1) of the formula (IV) in a total amount of 0.1 to 20% by weight, preferably 0.5 to 15% by weight and particularly preferably 2 to 8% by weight.

Even the addition of lesser amounts of water leads to hydrolysis in organic silicon compounds with at least one hydrolyzable group. The hydrolysis products and/or organic silicon compounds having at least one hydroxy group may react with each other in a condensation reaction. For this reason, both the organosilicon compounds having at least one hydrolyzable group and their hydrolysis and/or condensation products may be present in the agent (a). When organosilicon compounds having at least one hydroxyl group are used, both the organic silicon compounds having at least one hydroxyl group and their condensation products may be present in the agent (a).

A condensation product is understood to be a product formed by the reaction of at least two organic silicon compounds each having at least one hydroxyl group or hydrolyzable group per molecule with elimination of water and/or with elimination of an alkanol. The condensation products can be, for example, dimers, but also trimers or oligomers, with the condensation products being in equilibrium with the monomers. Depending on the amount of water used or consumed in the hydrolysis, the equilibrium shifts from monomeric organic silicon compounds to condensation product.

Particularly satisfactory results were obtained when organic silicon compounds (a1) of formula (I) and/or (II) were used in the process. Since, as already described above, hydrolysis/condensation already starts at traces of moisture, the hydrolysis and/or condensation products of the organic silicon compounds (I) and/or (II) are also included in this embodiment.

Particularly resistant stains could be obtained when using an alkaline adjusted agent (a). Preferably, agent (a) comprises water and has a pH of from 7 to 11.5, preferably from 7.5 to 11, and more preferably from 8 to 10.5.

In another very particularly preferred embodiment, the process is wherein the agent (a) has a pH of from 7 to 11.5, preferably from 7.5 to 11, and particularly preferably from 8 to 10.5.

Agent (b)

The agent (b) is exemplified by the presence of at least one color-imparting compound (b1) and at least one film-forming polymer (b2). The coloring compound (b1) comprises at least one effect pigment comprising i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal particle carrier layer.

In the effect pigments, interference colors with high chroma are developed by interference between the light reflected from the surface of the substrate platelet and the light reflected from the surfaces of the metal particles.

Accordingly, with the help of the "colored" effect pigments, keratin fibers can be dyed in particularly intensive and numerous color shades.

The effect pigment has a substrate platelet.

The substrate wafer may have a thickness in the range of 10 nm to 5,000 nm, preferably in the range of 20 nm to 1,000 nm. However, it may be preferred that the average thickness is at most 150 nm, preferably less than 50 nm, more preferably less than 30 nm, particularly preferably at most 25 nm, for example at most 20 nm. Preferably, each substrate plate has a thickness that is as uniform as possible.

The substrate plate is preferably monolithic. Monolithic in this context means comprising a single self-included unit without fractures, stratifications or inclusions, although microstructural changes may occur within the substrate platelet. The substrate platelet is preferably homogeneous in structure, i.e., no concentration gradient occurs within the platelet. In particular, the substrate platelet is not layered and does not have particles or particulates distributed therein.

The size of the substrate platelet can be tailored to the specific application, for example the desired effect on a keratinous material. Typically, the substrate platelets have an average largest diameter of about 2 to 300 μm, especially about 5 to 100 μm. The average size of the uncoated substrate platelets is the d50 value of the uncoated substrate platelets. Unless otherwise stated, the d50 value was determined using a Sympatec Helos device with quixel wet dispersion. To prepare the sample, the sample to be analyzed was pre-dispersed in isopropanol for 3 minutes.

The substrate platelet can be composed of any material that can be formed into platelet shape.

They can be of natural origin, but also synthetically produced. Materials from which the substrate platelets can be constructed include metals and metal alloys, metal oxides, preferably aluminum oxide, inorganic compounds and minerals such as mica and (semi-)precious stones, and plastics. Preferably, the substrate plates are constructed of a metal or alloy.

Any metal suitable for effect pigments can be used. Such metals include iron and steel, as well as all air- and water-resistant (semi)metals such as platinum, tin, zinc, chromium, molybdenum and silicon, as well as their alloys such as aluminum bronzes and brass. Preferred metals are aluminum, copper, silver and gold. Preferred substrate platelets include aluminum platelets and brass platelets, with aluminum substrate platelets being particularly preferred.

Substrate plates made of aluminum can be produced, among other things, by punching out of aluminum foil or according to common milling and atomization techniques. For example, aluminum flakes are available from the Hall process, a wet milling process.

Other metal flakes, for example of bronze, can be obtained in a dry grinding process such as the Hametag process.

The substrate plates can have different shapes. For example, lamellar or lenticular metal platelets or so-called vacuum metallized pigments (VMP) can be used as substrate platelets. Lamellar substrate platelets are exemplified by an irregularly structured edge and are also referred to as "cornflakes" due to their appearance. Lenticular substrate platelets have a regular round edge and are also referred to as "silverdollars" due to their appearance.

The metal or metal alloy substrate plates can be passivated, for example by anodizing (oxide layer) or chromating. In the case of a substrate plate made of aluminum, for example, this has a passivation layer comprising aluminum oxide.

The effect pigment has several layers. In particular, the effect pigment has at least a metal oxide (hydrate) layer ii) provided on the surface of the substrate wafer and a metal particle carrier layer iii) provided on the surface of the metal oxide (hydrate) layer.

These layers can change the surface properties and/or optical properties of the effect pigment and increase the mechanical and chemical load-bearing capacity of the effect pigments. For example, only the upper and/or lower side of the substrate wafer may be coated, with the side surfaces being recessed. Preferably, the entire surface of the optionally passivated substrate platelets, including the side surfaces, is covered by the further layers. The substrate platelets are preferably completely encased by the further layers.

A metal oxide (hydrate) layer ii) is provided on the surface of the substrate wafer. Suitable materials for the metal oxide (hydrate) layer ii) are all metal oxides (hydrates) that can be permanently applied to the substrate platelets in a film-like manner.

It is preferred that the metal oxide and/or metal oxide hydrate is selected from the group of silicon (di)oxide, silicon oxide hydrate, aluminum oxide, aluminum oxide hydrate, boron oxide, germanium oxide, manganese oxide, magnesium oxide, iron oxide, cobalt oxide, chromium oxide, titanium dioxide, vanadium oxide, zirconium oxide, tin oxide, zinc oxide and mixtures thereof.

It is particularly preferred that the metal oxide (hydrate) layer comprises ii) silicon dioxide, especially amorphous silicon dioxide.

The thickness of the metal oxide (hydrate) layer ii) is preferably in the range of 10 to 500 nm, more preferably in the range of 10 to 100 nm.

While the metal oxide (hydrate) layer ii) may be formed directly on the surface of the substrate wafer, another layer is preferably disposed between the substrate wafer and metal oxide (hydrate) layer ii) as an underlayer. The sublayer may comprise a molybdenum and/or phosphorus comprising oxide, hydroxide or hydrate. The thickness of the underlayer is preferably in the range of 0.5 to 10 nm. The underlayer may be present on the surface of the substrate plate in addition to a passivation layer or as an alternative to the passivation layer.

The metal oxide (hydrate), the silicon dioxide, can be applied wet-chemically, for example by the sol-gel process. This process comprises dispersing the uncoated substrate wafer or the already coated substrate wafer in a solution of a metal alkoxide such as tetraethyl orthosilicate or aluminum triisopropanolate (usually in a solution of organic solvent or a mixture of organic solvent and water with at least 50 wt. % organic solvent such as a C1 to C4 alcohol), and adding a weak base or acid to hydrolyze the metal alkoxide, thereby forming a film of the metal oxide (hydrate) on the surface of the (coated) substrate platelets.

A metal particle support layer iii) is provided on the surface of the metal oxide (hydrate) layer ii).

The metal particle support layer iii) comprises a metal layer and/or a metal oxide layer.

When the metal particle support layer iii) comprises a metal layer and a metal oxide layer, the arrangement of these layers is not limited. In particular, the metal particle support layer iii) may have a structure in which the metal layer is disposed on the surface of the metal oxide (hydrate) layer ii) and the metal oxide layer is disposed on the surface of the metal layer. The metal particle support layer iii) may also have a structure in which the metal oxide layer is disposed on the surface of the metal oxide (hydrate) layer ii) and the metal layer is disposed on the surface of the metal oxide layer. Further, the metal particle support layer iii) may also include two or more metal layers and/or two or more metal oxide layers. The arrangement of the layers is not limited here either.

It is preferred that the metal particle support layer iii) comprises at least one metal layer. It is further preferred that the metal layer comprises an element selected from tin (Sn), palladium (Pd), platinum (Pt) and gold (Au). In particular, the metal particle support layer iii) comprises at least one metal layer comprising an element selected from tin (Sn) and palladium (Pd).

While the metal particle support layer iii) may be formed directly on the surface of the metal oxide (hydrate) layer ii), another layer may be present between the metal oxide (hydrate) layer ii) and the metal particle support layer iii). This further layer may comprise, for example, an oxide or hydroxide of aluminum or cerium.

If the metal particle support layer iii) comprises a metal layer, the preparation can be carried out, for example, by employing a process for hydrolytic deposition of metal alkoxide by a sol-gel process or by employing a process in which alkali is added to a metal salt solution comprising the metal to form the metal layer of the metal particle support layer iii).

If the formation of the metallic particles is carried out by electroless plating, the metal particle support layer iii) is preferably formed by adding alkali to a metal salt solution comprising the metal for forming the metal layer of the metal particle support layer iii).

Tetraethoxytin or the like can be used as a metal alkoxide in the hydrolytic deposition of metal alkoxide. Ammonia water, ethylenediamine, monoethanolamine, diethanolamine, hydrazine, urea or the like can be used as hydrolytic catalyst.

Stannous chloride, stannous fluoride or the like can be used as a metal salt in the process in which, by adding alkali to a metal salt solution, the metal particle support layer iii) is formed. Ammonia water, sodium hydroxide solution, monoethanolamine, diethanolamine or the like may be used as alkali, and water, ethanol, isopropyl alcohol, methylpropylene glycol, butyl cellosolve or the like as solvent.

When the metal particles are formed by electroless plating with water-soluble metal salt, the metal layer of the metal particle support layer iii) may be formed by a process used as a pretreatment for electrolytic plating. These processes are, for example, the catalyst-accelerator process or the sensitizing-activating process. Likewise, only parts of the procedures, for example the catalyst procedure or only the sensitization procedure, can be carried out.

Water-soluble metal salt comprising Sn, Pd, Pt or Au can be used as a metal source for the preparation of the metal particle support layer iii) formed in the process used as a pretreatment for electroless plating. Tin chloride, tin oxalate, tin sulfate, tin bromide, tin acetate, tin boron fluoride, tin fluoride, sodium stannate, potassium stannate, tin mesylate, tin sulfide, palladium chloride, palladium acetate, palladium bromide, palladium hydroxide, palladium nitrate, palladium oxide, palladium sulfate, gold bromide, gold chloride, platinum chloride, platinum chloride, platinum oxide or the like are examples of the water-soluble metal salt.

If the metal particle support layer iii) comprises a metal oxide layer, it preferably does not contain silica. The metal particle support layer iii) in the form of a metal oxide layer preferably comprises an oxide of at least one element selected from the group of Mg (magnesium), Sn (tin), Zn (zinc), Co (cobalt), Ni (nickel), Fe (iron), Zr (zirconium), Ti (titanium), and Ce (cerium). Particularly preferably, the metal particle support layer iii) in the form of a metal oxide layer comprises a metal oxide of Sn, Zn, Ti and Ce. Very preferably, the metal particle support layer iii) in the form of a metal oxide layer comprises tin oxide.

The preparation of the one metal oxide layer of a metal particle support layer iii) may be carried out, for example, by hydrolyzing an alkoxide of a metal forming the metal of the metal oxide in a sol-gel process, adding an alkali to a metal salt solution of a metal forming the metal of the metal oxide, and bringing the coated substrate wafer into contact with a solution in which an organic metal compound has been dissolved in an organic solvent, and then heat-treating.

Suitable metal alkoxides that can be used in the process to deposit the metal oxide layer by hydrolysis include tetraethoxytin and tetrabutoxytitanium.

Examples of a metal salt that can be used in the process of depositing the metal oxide layer by neutralization with alkali include stannous chloride, stannous fluoride, zinc chloride, titanyl sulfide, cernitrate, and ceric acetate.

Examples of the organic metal compound include fatty acid metal salts such as cobalt naphthenate, nickel stearate, zirconium stearate and dibutyltin dilaurate.

The heat treatment temperature at which the organic metal compound is to be decomposed and oxidized is preferably 200° C. to 500° C.

The metal particles can be formed by electroless plating on the surface of the metal particle support layer iii). When the effect pigment provided with the metal particle support layer iii) is immersed in an electroless plating solution, a reducing agent in the plating solution is oxidized on the surface of the metal particle support layer iii) due to the catalytic activity of the metal particle support layer iii).

Metal ions in the electroless plating solution are reduced by the electrons emitted at this time, the metal is deposited on the surface of the metal particle support layer, and the metal particles are formed.

The thickness of the metal particle support layer iii) is preferably up to 30 nm and more preferably in the range of 0.1 to 10 nm.

Metal particles iv) are deposited on the surface of the metal particle support layer iii). In a preferred embodiment, the metal particles iv) directly cover a portion of the metal particle support layer iii). In this embodiment, the effect pigment has areas in which there are no metal particles, i.e., areas which are not covered with the metal particles.

The metal particles may comprise at least one element selected from the group of aluminum (Al), titanium (Ti), chromium (Cr), iron (Fe), cobalt (Co), nickel (Ni), copper (Cu), zinc (Zn), ruthenium (Ru), rhodium (Rh), palladium (Pd), silver (Ag), tin (Sn), platinum (Pt), gold (Au), and alloys thereof. It is particularly preferred that the metal particles comprise at least one element selected from copper (Cu), nickel (Ni) and silver (Ag). It is highly preferred that the metal particles comprise silver (Ag).

The average particle diameter of the metal particles is preferably not more than 50 nm, more preferably not more than 30 nm. The distance between the metal particles is preferably not more than 10 nm.

Suitable methods for forming the metal particles include vacuum evaporation, sputtering, chemical vapor deposition (CVD), electroless plating, or the like. Of these processes, electroless plating is particularly preferred.

The effect pigment may further have on the metal particles iv) a corrosion inhibition layer comprising a corrosion inhibitor. The corrosion inhibitor is preferably selected from the group of benzotriazoles, tetrazoles, imidazoles, alkylaminotriazoles, benzothiazoles, α- or β-dicarbonyl compounds and mercaptans.

Furthermore, the effect pigment may have on the metal particles iv) or on the surface of the corrosion inhibition layer a weathering resistant top layer comprising an oxide, a hydroxide or a hydrate of aluminum, silicon and/or cerium.

In addition, the effect pigment may have a covering resin layer or covering resin layer as the outermost layer.

Such effect pigments are available, for example, under the name Cosmicolor® Celeste from Toyal Europe. Suitable effect pigments include, for example Cosmicolor® Celeste Rose Pink, Cosmicolor® Celeste Iris Blue, Cosmicolor® Celeste Morpho Blue, Cosmicolor® CelesteTecla Green, Cosmicolor® Celeste Aqua Green, Cosmicolor® Celeste Meadow Gold, Cosmicolor® Celeste Ivy Orange, Cosmicolor® Celeste Cherry Pink und Cosmicolor® Celeste Maple Red.

Particularly satisfactory results could be obtained if the agent (a)—based on the total weight of the agent (a)—comprises one or more effect pigments in a total amount of 0.01 to 10% by weight, preferably 0.1 to 8% by weight, more preferably 0.2 to 6% by weight and very preferably 0.5 to 4.5% by weight.

In addition to the effect pigment, the agent (b) may comprise further colorant compounds selected from the group of pigments and/or direct dyes.

The agent (b) is further wherein it comprises at least one film-forming polymer (b2).

Polymers are macromolecules with a molecular weight of at least 1000 g/mol, preferably of at least 2500 g/mol, particularly preferably of at least 5000 g/mol, which include identical, repeating organic units. The polymers of the present disclosure may be synthetically produced polymers which are manufactured by polymerization of one type of monomer or by polymerization of several types of monomer which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. In terms of the present disclosure, it is preferred if the maximum molecular weight of the film-forming polymer (b) is not more than $10^7$ g/mol, preferably not more than $10^6$ g/mol, and particularly preferably not more than $10^5$ g/mol.

As contemplated herein, a film-forming polymer is a polymer which can form a film on a substrate, for example on a keratinic material or a keratinic fiber. The formation of a film can be demonstrated, for example, by viewing the polymer-treated keratinous material under a microscope.

The film-forming polymers (b2) in the agent (b) can be hydrophilic or hydrophobic.

In a first embodiment, it may be preferred to use at least one hydrophobic film-forming polymer in agent (b).

A hydrophobic polymer is a polymer that has a solubility in water at 25° C. (760 mmHg) of less than 1% by weight.

The water solubility of the film-forming, hydrophobic polymer can be determined in the following way, for example. 1 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than 1% by weight.

These include acrylic acid-type polymers, polyurethanes, polyesters, polyamides, polyureas, cellulose polymers, nitrocellulose polymers, silicone polymers, acrylamide-type polymers and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, a agent (b) is wherein it comprises at least one film-forming, hydrophobic polymer (b2) selected from the group of the copolymers of acrylic acid, the copolymers of methacrylic acid, the homopolymers or copolymers of acrylic acid esters, the homopolymers or copolymers of methacrylic acid esters homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming hydrophobic polymers, which are selected from the group of synthetic polymers, polymers obtainable by radical polymerization or natural polymers, have proved to be particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinyl amides, the esters or amides of (meth)acrylic acid having at least one $C_1$-$C_{20}$ alkyl group, an aryl group or a $C_2$-$C_{10}$ hydroxyalkyl group.

Other film-forming hydrophobic polymers may be selected from the homo- or copolymers of isooctyl (meth) acrylate, isononyl (meth)acrylate, 2-ethylhexyl (meth)acrylate, lauryl (meth)acrylate), isopentyl (meth)acrylate, n-butyl (meth)acrylate), isobutyl (meth)acrylate, ethyl (meth)acrylate, methyl (meth)acrylate, tert-butyl (meth) acrylate, stearyl (meth)acrylate, hydroxyethyl (meth)acrylate, 2-hydroxypropyl (meth)acrylate, 3-hydroxypropyl (meth)acrylate and/or mixtures thereof.

Further film-forming hydrophobic polymers can be selected from the homo- or copolymers of (meth)acrylamide, N-alkyl(meth)acrylamides, in those with C2-C18 alkyl groups, such as N-ethyl acrylamide, N-tert-butylacrylamide, le N-octylacrylamide, N-di(C1-C4)alkyl(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25 Methacrylate Copolymer), Structure 2001® (Acryla-tes/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme und Haas distributed Soltex OPT (Acrylates/C12-22 Alkyl methacrylate Copolymer).

Suitable polymers based on vinyl monomers may include, for example, the homopolymers and copolymers of N-vinylpyrrolidone, vinylcaprolactam, vinyl-(C1-C6)alkyl-pyrrole, vinyl oxazole, vinyl thiazole, vinyl pyrimidine or vinyl imidazole.

Also particularly suitable are the copolymers octylacrylamide/acrylates/butylaminoethyl methacrylate copolymer, such as those sold commercially by NATIONAL STARCH under the trade names AMPHOMER® or LOVOCRYL® 47, or the copolymers of acrylates/octylacrylamides sold under the trade names DERMACRYL® LT and DERMACRYL® 79 by NATIONAL STARCH.

Suitable olefin-based polymers include homopolymers and copolymers of ethylene, propylene, butene, isoprene and butadiene.

In another embodiment, the film-forming hydrophobic polymers may be the block copolymers comprising at least one block of styrene or the derivatives of styrene. These block copolymers may be copolymers comprising one or more blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

Surprisingly, it was found that particularly intense and washfast colorations could be obtained when agent (b) included at least one film-forming polymer (b2) selected from the group of acrylic acid homopolymers and copolymers, methacrylic acid homopolymers and copolymers, acrylic acid ester homopolymers and copolymers, methacrylic acid ester homopolymers and copolymers, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, a process is wherein the agent (b) comprises at least one film-forming polymer (b2) selected from the group of the homopolymers and copolymers of acrylic acid, the homopolymers and copolymers of methacrylic acid, the homopolymers and copolymers of acrylic acid esters, the homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further embodiment, it may be preferred to use at least one hydrophilic film-forming polymer (b2) in the agent (b).

A hydrophilic polymer is a polymer that has a solubility in water at 25° C. (760 mmHg) of more than 1% by weight, preferably more than 2% by weight.

The water solubility of the film-forming, hydrophilic polymer can be determined in the following way, for example. 1 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. A completely dissolved polymer appears macroscopically homogeneous. If the polymer-water mixture cannot be assessed visually due to a high turbidity of the mixture, the mixture is filtered. If no undissolved polymer remains on the filter paper, the solubility of the polymer is more than 1% by weight.

Nonionic, anionic and cationic polymers can be used as film-forming, hydrophilic polymers.

Suitable film-forming hydrophilic polymers may be selected, for example, from the group comprising polyvinylpyrrolidone (co)polymers, polyvinyl alcohol (co)polymers, vinyl acetate (co)polymers, the carboxyvinyl (co) polymers, the acrylic acid (co)polymers, the methacrylic acid (co)polymers, the natural gums, the polysaccharides and/or the acrylamide (co)polymers.

Furthermore, it is particularly preferred to use polyvinylpyrrolidone (PVP) and/or a vinylpyrrolidone-comprising copolymer as film-forming hydrophilic polymer.

In another very particularly preferred embodiment, an agent (b) is wherein it comprises at least one film-forming hydrophilic polymer selected from the group of polyvinylpyrrolidone (PVP) and the copolymers of polyvinylpyrrolidone.

It is further preferred if the agent comprises polyvinylpyrrolidone (PVP) as the film-forming hydrophilic polymer. Surprisingly, the wash fastness of the dyes obtained with PVP-comprising agents (b9 was also particularly good.

Particularly well-suited polyvinylpyrrolidones are available, for example, under the name Luviskol® K from BASF SE, especially Luviskol® K 90 or Luviskol® K 85 from BASF SE.

The polymer PVP K30, which is marketed by Ashland (ISP, POI Chemical), can also be used as another explicitly very well suited polyvinylpyrrolidone (PVP). PVP K 30 is a polyvinylpyrrolidone which is highly soluble in cold water and has the CAS number 9003-39-8. The molecular weight of PVP K 30 is about 40000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115 and available from BASF.

The use of film-forming hydrophilic polymers (b2) from the group of copolymers of polyvinylpyrrolidone has also led to particularly good and washfast color results.

Vinylpyrrolidone-vinyl ester copolymers, such as those marketed under the trademark Luviskol® (BASF), are particularly suitable film-forming hydrophilic polymers. Luviskol® VA 64 and Luviskol® VA 73, both vinylpyrrolidone/vinyl acetate copolymers, are particularly preferred non-ionic polymers.

Of the vinylpyrrolidone-comprising copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed under the name Luviskol® VA by BASF SE. For example, a VP/Vinyl Caprolactam/DMAPA Acrylates copolymer is sold under the trade name Aquaflex® SF-40 by Ashland Inc. For example, a VP/DMAPA acrylates copolymer is marketed by Ashland under the name Styleze CC-10 and is a highly preferred vinylpyrrolidone-comprising copolymer.

Other suitable copolymers of polyvinylpyrrolidone may also be those obtained by reacting N-vinylpyrrolidone with at least one further monomer from the group comprising V-vinylformamide, vinyl acetate, ethylene, propylene, acrylamide, vinylcaprolactam, vinylcaprolactone and/or vinyl alcohol.

In another very particularly preferred embodiment, an agent (b) is wherein it comprises at least one film-forming hydrophilic polymer (b2) selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another fussy copolymer of vinylpyrrolidone is the polymer known under the INCI designation maltodextrin/VP copolymer.

Furthermore, intensively colored keratinous material, especially hair, could be obtained with particularly good wash fastness properties when a nonionic film-forming hydrophilic polymer was used as the film-forming hydrophilic polymer.

In another embodiment, the agent (b) may comprise at least one nonionic film-forming hydrophilic polymer (b2).

As contemplated herein, a non-ionic polymer is understood to be a polymer which in a protic solvent—such as water—under standard conditions does not carry structural units with permanent cationic or anionic groups, which must be compensated by counterions while maintaining electron neutrality. Cationic groups include quaternized ammonium groups but not protonated amines. Anionic groups include carboxylic and sulphonic acid groups.

Preference is given to products comprising, as a nonionic, film-forming, hydrophilic polymer, at least one polymer selected from the group of Polyvinylpyrrolidone, Copolymers of N-vinylpyrrolidone and vinyl esters of carboxylic acids comprising 2 to 18 carbon atoms of N-vinylpyrrolidone and vinyl acetate, Copolymers of N-vinylpyrrolidone and N-vinylimidazole and methacrylamide, Copolymers of N-vinylpyrrolidone and N-vinylimidazole and acrylamide, Copolymers of N-vinylpyrrolidone with N,N-di(C1 to C4)alkylamino-(C2 to C4)alkyl acrylamide.

If copolymers of N-vinylpyrrolidone and vinyl acetate are used, it is again preferable if the molar ratio of the structural units included in the monomer N-vinylpyrrolidone to the structural units of the polymer included in the monomer vinyl acetate is in the range from 20:80 to 80:20, in particular from 30:70 to 60:40. Suitable copolymers of vinyl pyrrolidone and vinyl acetate are available, for example, under the trademarks Luviskol® VA 37, Luviskol® VA 55, Luviskol® VA 64 and Luviskol® VA 73 from BASF SE.

Another particularly preferred polymer is selected from the INCI designation VP/Methacrylamide/Vinyl Imidazole Copolymer, which is available under the trade name Luviset Clear from BASF SE.

Another particularly preferred nonionic, film-forming, hydrophilic polymer is a copolymer of N-vinylpyrrolidone and N,N-dimethylaminiopropylmethacrylamide, which is sold, for example, by ISP under the INCI designation VP/DMAPA Acrylates Copolymer, e.g., under the trade name Styleze® CC 10.

A cationic polymer is the copolymer of N-vinylpyrrolidone, N-vinylcaprolactam, N-(3-dimethylaminopropyl) methacrylamide and 3-(methacryloylamino)propyl-lauryl-dimethylammonium chloride (INCI designation: Polyquaternium-69), which is marketed, for example, under the trade name AquaStyle® 300 (28-32 wt. % active substance in ethanol-water mixture, molecular weight 350000) by ISP.

Other suitable film-forming, hydrophilic polymers include

Vinylpyrrolidone-vinylimidazolium methochloride copolymers, as offered under the designations Luviquat® FC 370, FC 550 and the INCI designation Polyquaternium-16 as well as FC 905 and HM 552, Vinylpyrrolidone-vinylcaprolactam-acrylate terpolymers, as they are commercially available with acrylic acid esters and acrylic acid amides as a third monomer component, for example under the name Aquaflex® SF 40.

Polyquaternium-11 is the reaction product of diethyl sulphate with a copolymer of vinyl pyrrolidone and dimethylaminoethyl methacrylate. Suitable commercial products are available under the names Dehyquart® CC 11 and Luviquat® PQ 11 PN from BASF SE or Gafquat 440, Gafquat 734, Gafquat 755 or Gafquat 755N from Ashland Inc.

Polyquaternium-46 is the reaction product of vinylcaprolactam and vinylpyrrolidone with methylvinylimidazolium methosulfate and is available for example under the name Luviquat® Hold from BASF SE. Polyquaternium-46 is preferably used in an amount of 1 to 5% by weight—based on the total weight of the cosmetic composition. It particularly prefers to use polyquaternium-46 in combination with a cationic guar compound. It is even highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names Carbopol 980, 981, 954, 2984 and 5984 by Lubrizol or under the names Synthalen M and Synthalen K by 3V Sigma (The Sun Chemicals, Inter Harz).

Examples of suitable film-forming, hydrophilic polymers from the group of natural gums are xanthan gum, gellan gum, carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamides are, for example, polymers prepared from monomers of (meth)acrylamido-C1-C4-alkyl sulfonic acid or salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2- methylpropanesulfonic acid and/or poly-2-methylacrylamido-n-butanesulfonic acid.

Preferred polymers of poly(meth)arylamido-C1-C4-alkyl-sulfonic acids are crosslinked and at least 90% neutralized. These polymers can be crosslinked or non-crosslinked.

Cross-linked and fully or partially neutralized polymers of the poly-2-acrylamido-2-methylpropane sulfonic acid type are available under the INCI names "Ammonium Polyacrylamido-2-methyl-propanesulphonates" or "Ammonium Polyacryldimethyltauramides".

Another preferred polymer of this type is the crosslinked poly-2-acrylamido-2methyl-propanesulfonic acid polymer sold by Clariant under the trade name Hostacerin AMPS, which is partially neutralized with ammonia.

In another explicitly very particularly preferred embodiment, a process is wherein the agent (b) comprises at least one anionic, film-forming, polymer (b2).

In this context, the best results were obtained when the agent (b) comprises at least one film-forming polymer (b2) comprising at least one structural unit of formula (P-I) and at least one structural unit of formula (P-II)

(P-I)

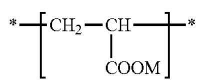

(P-II)

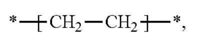

where

M is a hydrogen atom or ammonium ($NH_4$), sodium, potassium, ½ magnesium or ½ calcium.

In another preferred embodiment, a method is wherein the agent (b) comprises at least one film-forming polymer (b2) comprising at least one structural unit of formula (P-I) and at least one structural unit of formula (P-II)

(P-I)

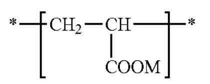

(P-II)

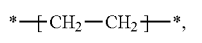

where

M is a hydrogen atom or ammonium ($NH_4$), sodium, potassium, ½ magnesium or ½ calcium.

If M represents a hydrogen atom, the structural unit of the formula (P-I) is based on an acrylic acid unit.

If M stands for an ammonium counterion, the structural unit of the formula (P-I) is based on the ammonium salt of acrylic acid.

If M stands for a sodium counterion, the structural unit of the formula (P-I) is based on the sodium salt of acrylic acid.

If M stands for a potassium counterion, the structural unit of the formula (P-I) is based on the potassium salt of acrylic acid.

If M stands for a half equivalent of a magnesium counterion, the structural unit of the formula (P-I) is based on the magnesium salt of acrylic acid.

If M stands for a half equivalent of a calcium counterion, the structural unit of the formula (P-I) is based on the calcium salt of acrylic acid.

The film-forming polymer or polymers (b2) are preferably used in certain ranges of amounts in the agent (b). In this context, it has proved particularly preferable for solving the problem as contemplated herein if the agent (b) comprises—based on the total weight of the agent (b)—one or more film-forming polymers (b2) in a total amount of from 0.1 to 18% by weight, preferably from 1 to 16% by weight, more preferably from 5 to 14.5% by weight and very particularly preferably from 8 to 12% by weight.

In a further preferred embodiment, a process is wherein the agent (b) comprises—based on the total weight of the agent (b)—one or more film-forming polymers (b2) in a total amount of from 0.1 to 18% by weight, preferably from 1 to 16% by weight, more preferably from 5 to 14.5% by weight and very particularly preferably from 8 to 12% by weight.

Other Ingredients in Agents (a) and (b)

The agents (a) and (b) described above may also contain one or more optional ingredients.

It is particularly preferred that the agent (a) used in the dyeing process comprises at least one colorant compound (a2) selected from the group of pigments and/or direct dyes.

The use of pigments has proved to be particularly preferable in this context.

In another very particularly preferred embodiment, a process is wherein the agent (a) comprises at least one colorant compound (a2) from the group comprising pigments.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable Pigments can be of Inorganic and/or Organic Origin.

In a preferred embodiment, a process is wherein the agent (a) comprises at least one colorant compound (a2) from the group comprising inorganic and/or organic pigments.

Preferred pigments are selected from synthetic or natural inorganic pigments. Inorganic pigments of natural origin can be produced, for example, from chalk, ochre, umber, green earth, fired Terra di Siena or graphite. Furthermore, black pigments such as iron oxide black, colored pigments such as ultramarine or iron oxide red, and fluorescent or phosphorescent pigments can be used as inorganic pigments.

Particularly suitable are colored metal oxides, hydroxides and oxide hydrates, mixed-phase pigments, sulfur-comprising silicates, silicates, metal sulfides, complex metal cyanides, metal sulphates, chromates and/or molybdates. Particularly preferred pigments are black iron oxide (CI 77499), yellow iron oxide (CI 77492), red and brown iron oxide (CI 77491), manganese violet (CI 77742), ultramarines (sodium aluminum sulfosilicates, CI 77007, Pigment Blue 29), chromium oxide hydrate (CI77289), iron blue (ferric ferrocyanide, C177510) and/or carmine (cochineal).

Also particularly preferred pigments are colored pearlescent pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

Also preferred mica-based pigments are synthetically produced mica platelets coated with metal oxide, based on synthetic fluorophlogopite (INCI: Synthetic Fluorphlogopite). The synthetic fluorophlogopite platelets are coated, for example, with tin oxide, iron oxide(s) and/or titanium dioxide. The metal oxide layers may further contain pigments such as ferric hexacyanidoferrate(II/III) or carmine red. Such mica pigments are available, for example, under the name SYNCRYSTAL from Eckart.

Accordingly, a preferred process is wherein the agent (a) comprises at least one colorant compound (a2) from the group of pigments selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, the process is wherein the agent (a) comprises at least one colorant compound (a2) from the group of pigments selected from mica- or mica-based pigments which are reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Other suitable pigments are based on metal oxide-coated platelet-shaped borosilicates. These are coated with tin oxide, iron oxide(s), silicon dioxide and/or titanium dioxide, for example. Such borosilicate-based pigments are available, for example, under the name MIRAGE from Eckart or Reflecks from BASF SE.

Examples of particularly suitable pigments are commercially available under the trade names Rona®, Colorona®, Xirona®, Dichrona® and Timiron® from Merck, Ariabel® and Unipure® from Sensient, Prestige® from Eckart Cosmetic Colors, Flamenco®, Cellini®, Cloisonné®, Duocrome®, Gemtone®, Timica®, MultiReflections, Chione from BASF SE and Sunshine® from Sunstar.

Very particularly preferred pigments with the trade name Colorona® are, for example:

Colorona Copper, Merck, MICA, CI 77491 (IRON OXIDES)

Colorona Passion Orange, Merck, Mica, CI 77491 (Iron Oxides), Alumina

Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES)

Colorona Dark Blue, Merck, MICA, TITANIUM DIOXIDE, FERRIC FERROCYANIDE

Colorona Chameleon, Merck, CI 77491 (IRON OXIDES), MICA

Colorona Aborigine Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE)

Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D&C RED NO. 30 (CI 73360)

Colorona Majestic Green, Merck, CI 77891 (TITANIUM DIOXIDE), MICA, CI 77288 (CHROMIUM OXIDE GREENS)

Colorona Light Blue, Merck, MICA, TITANIUM DIOXIDE (CI 77891), FERRIC FERROCYANIDE (CI 77510)

Colorona Red Gold, Merck, MICA, CI 77891 (TITANIUM DIOXIDE), CI 77491 (IRON OXIDES)

Colorona Gold Plus MP 25, Merck, MICA, TITANIUM DIOXIDE (CI 77891), IRON OXIDES (CI 77491)

Colorona Carmine Red, Merck, MICA, TITANIUM DIOXIDE, CARMINE

Colorona Blackstar Green, Merck, MICA, CI 77499 (IRON OXIDES)

Colorona Bordeaux, Merck, MICA, CI 77491 (IRON OXIDES)

Colorona Bronze, Merck, MICA, CI 77491 (IRON OXIDES)

Colorona Bronze Fine, Merck, MICA, CI 77491 (IRON OXIDES)

Colorona Fine Gold MP 20, Merck, MICA, CI 77891 (TITANIUM DIOXIDE), CI 77491 (IRON OXIDES)

Colorona Sienna Fine, Merck, CI 77491 (IRON OXIDES), MICA

Colorona Sienna, Merck, MICA, CI 77491 (IRON OXIDES)

Colorona Precious Gold, Merck, Mica, CI 77891 (Titanium dioxide), Silica, CI 77491 (Iron oxides), Tin oxide Colorona Sun Gold Sparkle MP 29, Merck, MICA, TITANIUM DIOXIDE, IRON OXIDES, MICA, CI 77891, CI 77491 (EU)

Colorona Mica Black, Merck, CI 77499 (Iron oxides), Mica, CI 77891 (Titanium dioxide)

Colorona Bright Gold, Merck, Mica, CI 77891 (Titanium dioxide), CI 77491 (Iron oxides)

Colorona Blackstar Gold, Merck, MICA, CI 77499 (IRON OXIDES)

Colorona SynCopper, Merck, Synthetic Fluorphlogopite (and) Iron Oxides

Colorona SynBronze, Merck, Synthetic Fluorphlogopite (and) Iron Oxides

Further particularly preferred pigments with the trade name Xirona® are, for example:

Xirona Golden Sky, Merck, Silica, CI 77891 (Titanium Dioxide), Tin Oxide

Xirona Caribbean Blue, Merck, Mica, CI 77891 (Titanium Dioxide), Silica, Tin Oxide Xirona Kiwi Rose, Merck, Silica, CI 77891 (Titanium Dioxide), Tin Oxide Xirona Magic Mauve, Merck, Silica, CI 77891 (Titanium Dioxide), Tin Xirona Le Rouge, Merck, Iron Oxides (and) Silica In addition, particularly preferred pigments with the trade name Unipure® are, for example:

Unipure Red LC 381 EM, Sensient CI 77491 (Iron Oxides), Silica

Unipure Black LC 989 EM, Sensient, CI 77499 (Iron Oxides), Silica

Unipure Yellow LC 182 EM, Sensient, CI 77492 (Iron Oxides), Silica

Also particularly preferred pigments with the trade name Flamenco® are, for example:

Flamenco® Summit Turquoise T30D, BASF, Titanium Dioxide (and) Mica

Flamenco® Super Violet 530Z, BASF, Mica (and) Titanium Dioxide

In a further embodiment, the agent (a) used in the process may also contain one or more colorant compounds (a2) from the group of organic pigments.

The organic pigments are correspondingly insoluble organic dyes or colorants which may be selected, for example, from the group of nitroso, nitro-azo, xanthene, anthraquinone, isoindolinone, isoindoline, quinacridone, perinone, perylene, diketopyrrolopyorrole, indigo, thioindido, dioxazine and/or triarylmethane compounds.

Examples of particularly suitable organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, the process is wherein the composition (a) comprises at least one colorant compound (a2) from the group of organic pigments selected from the group of carmine, quinacridone, phthalocyanine, sorghum, blue pigments having the color index numbers Cl 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Also, suitable colorant compounds (a2) from the group of pigments are inorganic and/or organic pigments modified with a polymer. The polymer modification can, for example, increase the affinity of the pigments for the film formed by the organic silicon compound (a1) on the keratinous material.

Other effect pigments, such as metallic luster pigments, can also be used as colorant compound (a2).

The effect pigments may include, for example, pigments based on a lamellar substrate platelet, pigments based on lenticular substrate platelets, pigments based on substrate platelets comprising "vacuum metallized pigments" (VMP).

Suitable effect pigments include, for example, the pigments Alegrace® Marvelous, Alegrace© Gorgeous or Alegrace® Aurous from Schlenk Metallic Pigments.

Also, suitable effect pigments are the aluminum-based pigments of the SILVERDREAM series and the pigments of the VISIONAIRE series from Eckart, which are based on aluminum or on copper/zinc-comprising metal alloys.

Other suitable effect pigments are based on metal oxide-coated platelet-shaped borosilicates. These are coated with tin oxide, iron oxide(s), silicon dioxide and/or titanium dioxide, for example. Such borosilicate-based pigments are available, for example, under the name MIRAGE from Eckart or Reflecks from BASF SE.

Due to their excellent light and temperature stability, the use of the above pigments in agent (a) is particularly preferred. It is also preferred if the pigments used have a certain particle size. This particle size leads on the one hand to an even distribution of the pigments in the formed polymer film and on the other hand avoids a rough hair or skin feeling after application of the cosmetic product. As contemplated herein, it is therefore advantageous if the at least one pigment has an average particle size $D_{50}$ of 1 to 50 μm, preferably 5 to 45 μm, preferably 10 to 40 μm, 14 to 30 μm. The mean particle size $D_{50}$, for example, can be determined using dynamic light scattering (DLS).

In a further preferred embodiment, the process is wherein the agent (a) comprises—based on the total weight of the agent (a)—one or more colorant compound(s) (a2) in the form of pigments in a total amount of from 0.01 to 10% by weight, preferably from 0.1 to 8% by weight, more preferably from 0.2 to 6% by weight and very particularly preferably from 0.5 to 4.5% by weight.

As colorant compound(s) (a2), the agents (a) used in the process may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments.

Preferably, the direct dyes within the meaning of the present disclosure have a solubility in water (760 mmHg) at 25° C. of more than 1 g/L.

Direct dyes can be divided into anionic, cationic and non-ionic direct dyes.

In a further preferred embodiment, the process is wherein the agent (a) further comprises as coloring compound (a2) at least one anionic, cationic and/or nonionic direct dye.

In a further preferred embodiment, the process is wherein the agent (a) further comprises at least one colorant compound (a2) selected from the group of anionic, nonionic, and/or cationic direct dyes.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

As non-ionic direct dyes, non-ionic nitro and quinone dyes and neutral azo dyes can be used. Suitable non-ionic direct dyestuffs are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4, 6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

In the course of the work leading to the present disclosure, it has been found that dyeing's of particularly high color intensity can be produced with agents (a) comprising at least one anionic direct dye.

In an explicitly quite particularly preferred embodiment, the process is therefore wherein the agent (a) further comprises at least one anionic direct dye as colorant compound (a2).

Anionic direct dyes are also called acid dyes. Acid dyes are direct dyes that have at least one carboxylic acid group (—COOH) and/or one sulphonic acid group (—$SO_3$H). Depending on the pH value, the protonated forms (—COOH, —$SO_3$H) of the carboxylic acid or sulphonic acid groups are in equilibrium with their deprotonated forms (—$OO^-$, —$SO_3$— present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. The acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In one embodiment, a process for dyeing keratinous material is thus preferred, which is wherein the composition (a) further comprises at least one anionic direct dye as coloring compound (a2), which is selected from the group of nitrophenylenediamines, nitroaminophenols, azo dyes, anthraquinone dyes, triarylmethane dyes, xanthene dyes, rhodamine dyes, oxazine dyes and/or indophenol dyes, the xanthene dyes, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—$SO_3$H), a sodium sulfonate group (—$SO_3$H) and/or a potassium sulfonate group (—$SO_3$K).

For example, one or more compounds from the following group can be selected as particularly well suited acid dyes: Acid Yellow 1 (D&C Yellow 7, Citronin A, Ext. D&C Yellow No. 7, Japan Yellow 403, CI 10316, COLIPA no. B001), Acid Yellow 3 (COLIPA no: C 54, D&C Yellow No. 10, Quinoline Yellow, E104, Food Yellow 13), Acid Yellow 9 (CI 13015), Acid Yellow 17 (CI 18965), Acid Yellow 23 (COLIPA no. C 29, Covacap Jaune W 1100 (LCW), Sicovit Tartrazine 85 E102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no. C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Real red D, FD&C Red Nr. 2, Food Red 9, Naphthol red S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no. 106 Pontacyl Brilliant Pink), Acid Red 73 (CI 27290), Acid Red 87 (Eosin, CI 45380), Acid Red 92 (COLIPA no. C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no. 2, C.I. 60730, COLIPA no. C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no. 401, Naphthalene Black 10B, Amido Black 10B, CI 20 470, COLIPA no. B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trisodium salt of 7-hydroxy-8-[(E)-(4-sulfonato-1-naphthyl)-diazenyl)]-1,3-naphthalenedisulfonate and has a remarkably high water solubility of more than 20% by weight.

Acid Red 33 is the disodium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a solubility in water of more than 20% by weight (25° C.).

A highly preferred process is therefore wherein the agent (a) comprises at least one first colorant compound (a2) from the group of anionic direct dyes selected from the group of Acid Yellow 1, acid yellow 3, acid yellow 9, acid yellow 17, acid yellow 23, acid yellow 36, acid yellow 121, acid orange 6, acid orange 7, acid orange 10, acid orange 11, acid orange 15, acid orange 20, acid orange 24, acid red 14, acid red 27, acid red 33, acid red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s), in particular the anionic direct dyes, can be used in different amounts in the medium (a) depending on the desired color intensity. Particularly satisfactory results were obtained when the agent (a) comprises—based on its total weight—one or more direct dyes (a2) in a total amount of from 0.01 to 10% by weight, preferably from 0.1 to 8% by weight, more preferably from 0.2 to 6% by weight and very particularly preferably from 0.5 to 4.5% by weight.

In a further preferred embodiment, the process is wherein the agent (a)—based on the total weight of the agent (a)—further comprises one or more direct dyes as colorant compound (a2) in a total amount of from 0.01 to 10% by weight, preferably from 0.1 to 8% by weight, more preferably from 0.2 to 6% by weight and very preferably from 0.5 to 4.5% by weight.

The products may also contain one or more surfactants. The term surfactants refer to surface-active substances. A distinction is made between anionic surfactants comprising a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one $—COO^{(-)}—$ or $—SO_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, in addition to a $C_8$-$C_{24}$ alkyl or acyl group in the molecule, contain at least one free amino group and at least one —COOH or $—SO_3H$ group and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino-propionates, aminoglycinate, imidazoliniumbetaines and sulfobetaines.

Particularly preferred ampholytic surfactants are N-cocosalkylaminopropionate, cocosacylaminoethylaminopropionate and $C_{12}$-$C_{18}$-acylsarcosine.

The products may also additionally contain at least one non-ionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with suitable properties are also obtained if they contain as non-ionic surfactants fatty acid esters of ethoxylated glycerol reacted with at least 2 mol ethylene oxide.

In addition, the products may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually comprising a hydrocarbon backbone (e.g., comprising one or two linear or branched alkyl chains) and the positive charge(s) being in the hydrophilic head group. Examples of cationic surfactants are quaternary ammonium compounds which may carry one or two alkyl chains with a chain length of 8 to 28 carbon atoms as hydrophobic radicals, quaternary phosphonium salts substituted by one or more alkyl chains having a chain length of 8 to 28 carbon atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of 0.1 to 45 wt. %, preferably 1 to 30 wt. % and most preferably 1 to 15 wt. %—based on the total weight of the respective agent.

Furthermore, the agents may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of 0.1 to 45 wt. %, preferably 1 to 30 wt. % and most preferably 1 to 15 wt. %—based on the total weight of the respective agent.

To adjust the desired pH value, agents (a) and (b) may also contain at least one alkalizing agent and/or acidifying agent. The pH values for the purposes of the present disclosure are pH values measured at a temperature of 22° C.

As alkalizing agents, agents (a) and (b) may contain, for example, ammonia, alkanolamines and/or basic amino acids.

The alkanolamines that can be used in the compositions are preferably selected from primary amines having a $C_2$-$C_6$ alkyl parent carrying at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Particularly preferred alkanolamines are selected from 2-aminoethan-1-ol and/or 2-amino-2-methylpropan-1-ol. A particularly preferred embodiment is therefore wherein an agent (a) and/or (b) comprises as alkalizing agent an alkanolamine selected from 2-aminoethan-1-ol and/or 2-amino-2-methylpropan-1-ol.

For the purposes of the present disclosure, an amino acid is an organic compound comprising in its structure at least one protonatable amino group and at least one —COOH or one —$SO_3H$ group. Preferred amino acids are aminocarboxylic acids, especially α-(alpha)-aminocarboxylic acids and ω-aminocarboxylic acids, whereby α-aminocarboxylic acids are particularly preferred.

As contemplated herein, basic amino acids are those amino acids which have an isoelectric point pI of greater than 7.

Basic α-aminocarboxylic acids contain at least one asymmetric carbon atom. In the context of the present disclosure, both enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, omithine and histidine, especially preferably arginine and lysine. In a further particularly preferred embodiment, an agent is therefore wherein the alkalizing agent is a basic amino acid selected from the group of arginine, lysine, omithine and/or histidine.

In addition, agents (a) and/or (b) may contain further alkalizing agents, in particular inorganic alkalizing agents. Applicable inorganic alkalizing agents are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Very particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, omithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Acidifiers familiar to the skilled person are, for example, organic acids, such as citric acid, acetic acid, maleic acid, lactic acid, malic acid or tartaric acid, and dilute mineral acids, such as hydrochloric acid, sulfuric acid or phosphoric acid.

The agent (a) and/or agent (b) may further comprise a matting agent. Suitable matting agents include, for example, (modified) starches, waxes, talc and/or (modified) silicas. The amount of matting agent is preferably between 0.1 and 10% by weight based on the total amount of agent (a) or agent (b). Preferably, agent (b) comprises a matting agent.

The agents (a) and/or (b) may also contain other active ingredients, auxiliaries and additives, such as solvents; fatty ingredients such as $C_8$-$C_{30}$ fatty acid triglycerides, $C_8$-$C_{30}$ fatty acid monoglycerides, $C_8$-$C_{30}$ fatty acid diglycerides and/or hydrocarbons; polymers; structurants such as glucose or sodium chloride, hair conditioning compounds such as phospholipids, for example lecithin and kephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosenes; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliaries are preferably used in the agents (a) and/or (b) in amounts of from 0.0001 to 25% by weight in each case, from 0.0005 to 15% by weight, based on the total weight of the respective agent.

Process for Dyeing Keratinous Materials

In the process, agents (a) and (b) are applied to the keratinous materials, especially human hair. Thus, agents (a) and (b) are the ready-to-use agents. The agents (a) and (b) are different.

In principle, agents (a) and (b) can be applied simultaneously or successively, whereby successive application is preferred.

The best results were obtained when agent (a) was applied to the keratinous materials as a pretreatment agent and then agent (b) was applied as a coloring agent.

Therefore, a method for dyeing keratinous material, in particular human hair, comprising the following steps in the order given is particularly preferred:

in a first step, applying an agent (a) to the keratinous material, the agent (a) comprising at least one organic silicon compound (a1), and In a second step, applying an agent (b) to the keratinous material, the agent comprising (b):

(b1) at least one coloring compound comprising at least one effect pigment comprising i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal layer, and (b2) at least one film-forming polymer.

Moreover, to impart a high leaching resistance to the dyed keratinous material over a longer period, agents (a) and (b) are applied within the same dyeing process, which means that there is a period of a maximum of several hours between the application of agents (a) and (b).

In a further preferred embodiment, the method is wherein agent (a) is applied first and agent (b) is applied thereafter, the period between the application of agents (a) and (b) being at most 24 hours, preferably at most 12 hours and particularly preferably at most 6 hours.

In the process, the keratinous materials, in particular human hair, are first treated with agent (a). Subsequently, the actual colorant (b)—which comprises the colorant compounds—is applied to the keratinous materials.

A characteristic feature of the pretreatment agent (a) is its content of at least one reactive organic silicon compound. The reactive organic silicon compound(s) (a) functionalize the hair surface as soon as they meet it. In this way, a first film is formed. In the second step of the process, a colorant (b) is now applied to the hair. During application of the colorant (b), the colorant compounds interact with the film formed by the organosilicon compounds and are thus bound to the keratinous materials.

In the context of a further form of execution, a procedure comprising the following steps in the order indicated is particularly preferred Application of the agent (a) on the keratinous material, Allow the agent (a) to act for a period of 10 seconds to 10 minutes, preferably from 10 seconds to 5 minutes, if necessary, rinse the keratinous material with water, Application of agent (b) on the keratinous material, Allow the agent (b) to act for a period of 30 seconds to 30 minutes, preferably from 30 seconds to 10 minutes, and Rinse the keratinous material with water.

The rinsing of the keratinous material with water in steps (3) and (6) of the process is understood, as contemplated herein, to mean that only water is used for the rinsing process, without any other agents other than agents (a) and (b).

In step (1), agent (a) is first applied to the keratinous materials, in particular human hair.

After application, the agent (a) is left to act on the keratinous materials. In this context, exposure times of 10 seconds to 10 minutes, preferably 20 seconds to 5 minutes and most preferably 30 seconds to 2 minutes to the keratinous materials, to human hair, have proven to be particularly advantageous.

In a preferred embodiment of the process, the agent (a) can now be rinsed from the keratinic materials before the agent (b) is applied to the hair in the subsequent step.

Stains with equally good wash fastnesses were obtained when agent (b) was applied to the keratinous materials that were still exposed to agent (a).

In step (4), agent (b) is now applied to the keratinous materials. After application, let the agent (b) act on the hair.

Even with a short contact time of the agent (b), the process allows the production of dyeing's with particularly good intensity and wash fastness. Contact times of 10 seconds to 10 minutes, preferably 20 seconds to 5 minutes and most preferably 30 seconds to 3 minutes on the keratinous materials, on human hair, have proven to be particularly advantageous.

In step (6), the agent (b) (and any agent (a) still present) is now rinsed out of the keratinous material with water.

Multi-Component Packaging Unit (Kit-of-Parts)

In the process, agents (a) and (b) are applied to the keratinous materials, i.e., the two agents (a) and (b) are respectively the ready-to-use agents.

To increase user comfort, the user is preferably provided with all required resources in the form of a multi-component packaging unit (kit-of-parts).

A second subject of the present disclosure is therefore a multi-component packaging unit (kit-of-parts) for coloring keratinous material, comprehensively packaged separately from one another a first container comprising an agent (a), the agent (a) comprising at least one organic silicon compound (a1), and a second container comprising an agent (b), wherein the agent comprises (b):

(b1) at least one coloring compound comprising at least one effect pigment comprising i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal layer, and (b2) at least one film-forming polymer.

The organic silicon compounds included in agent (a) of the kit correspond to the organic silicon compounds that were also used in agent (a) of the method described above.

The colorant compounds selected from the group of effect pigments comprising i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal layer included in agents (b) of the kit, corresponding to the coloring compounds selected from the group of effect pigments comprising i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal layer, which have also been used in agents (b) of the method described above.

Agent (a) comprises, with the organic silicon compound(s), a class of reactive compounds capable of undergoing hydrolysis and/or oligomerization and/or polymerization in the presence of water as previously described. As a result of their high reactivity, these organic silicon compounds form a film on the keratinous material.

To avoid premature hydrolysis, oligomerization and/or polymerization, it may be preferable to prepare the ready-to-use agent (a) only shortly before use.

In the context of a further embodiment, a multi-component packaging unit (kit-of-parts) for coloring keratinic material is preferably packaged separately from one another a first container comprising an agent (a'), wherein the agent (a') comprises at least one organic silicon compound, a second container comprising an agent (a"), the agent (a") comprising water, and a third container comprising an agent (b), wherein the agent comprises (b):

(b1) at least one coloring compound comprising at least one effect pigment comprising i) a substrate platelet, ii) a metal oxide (hydrate) layer provided on the surface of the substrate platelet, iii) a metal particle carrier layer provided on the surface of the metal oxide (hydrate) layer, and iv) metal particles provided on the surface of the metal particle carrier layer, and (b2) at least one film-forming polymer.

To be able to provide a formulation that is as stable as possible in storage, the agent (a') itself is preferably formulated to be low in water or water-free.

In a preferred embodiment, a multicomponent packaging unit (kit-of-parts) is wherein the agent (a')—based on the total weight of the agent (a')—has a water content of less than 10% by weight, preferably of less than 5% by weight, more preferably of less than 1% by weight, still more preferably of less than 0.1% by weight and very particularly preferably of less than 0.01% by weight.

The agent (a") comprises water. In a preferred embodiment, a multicomponent packaging unit (kit-of-parts) is wherein the agent (a")—based on the total weight of the agent (a")—has a water content of from 15 to 100% by weight, preferably from 35 to 100% by weight, more preferably from 55 to 100% by weight, still more preferably from 65 to 100% by weight and very particularly preferably from 75 to 100% by weight.

Within this embodiment, the ready-to-use agent (a) is now prepared by mixing agents (a') and (a").

For example, the user may first stir or shake the agent (a') comprising the organic silicon compound(s) with the water-comprising agent (a"). The user can now apply this mixture of (a') and (a") to the keratinous materials—either immediately after its preparation or after a short reaction time of 10 seconds to 20 minutes. Afterwards, the user can apply agent (b) as described above.

In this embodiment of the multicomponent packaging unit, it may be preferred that the agent (a") further comprises at least one color-imparting compound (a2). This is preferably selected from the group of colored metal oxides, metal hydroxides, metal oxide hydrates, silicates, metal sulfides, complex metal cyanides, metal sulfates, bronze pigments and/or colored mica- or mica-based pigments coated with at least one metal oxide and/or a metal oxychloride.

Alternatively, multicomponent packaging unit may further comprise an agent (a") comprising at least one coloring compound (a2). Preferably, the agent (a") further comprises a silicone polymer.

Within this embodiment, the ready-to-use agent (a) is now prepared by mixing agents (a'), (a") and (a"').

Regarding the further preferred embodiments of the multicomponent packaging unit, the same applies mutatis mutantis as to the process.

EXAMPLES

1. Formulations

The following formulations have been produced (unless otherwise indicated, all figures are in % by weight)

| Pretreatment agent, agent (a) | |
|---|---|
| (3-Aminopropyl)triethoxysilane | 2.0 |
| Methyltrimethoxysilane | 7.0 |
| Ammonia/citric acid | ad pH 9.5 |
| Water | ad 100 |

The silanes were mixed with a portion of water, this mixture was left for 30 minutes. Then the pH value was adjusted to the desired value by adding citric acid/ammonia. Water was then added to make up to 100 g.

| Dye, agent (b) | |
|---|---|
| Cosmicolor ® Celeste Cherry Pink | 1 |
| PVP K 30 (Ashland, ISP, Polyvinylpyrrolidone) | 4.5 |
| Dermacryl 79 (Akzo Nobel, Acrylates/Octylacrylamide Copolymer, CAS-Nr. 129702-02-9) | 4.5 |
| Ammonia (25% aqueous solution) | ad pH 10 |
| Water | ad 100 |

2. Application

One strand of hair (Kerling, Euronatural hair white) was dipped into the medium (a) and left in it for 1 minute. Afterwards, excess agent (a) was stripped from each strand of hair. Each strand of hair was briefly washed with water. Excess water was scraped off each strand of hair.

Subsequently, the hair strands were each dipped in the agent (b) and left in it for 1 minute. Afterwards, excess agent (b) was stripped from each strand of hair. Each strand of hair was briefly washed with water. Excess water was scraped off each strand of hair.

Subsequently, the strands were visually evaluated

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for dyeing keratinous material, the method comprising the steps of:

applying an agent (a) to the keratinous material, wherein the agent (a) comprises:

(a1) at least one organic silicon compound of the formula (I) and at least one organic silicon compound of the formula (IV),

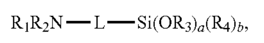

(I)

wherein $R_1$, $R_2$ independently represent a hydrogen atom or a $C_1$-$C_6$ alkyl group, L is a linear or branched, bivalent $C_1$-$C_{20}$ alkylene group, $R_3$ is a hydrogen atom or a $C_1$-$C_6$ alkyl group, $R_4$ stands for a $C_1$-$C_6$ alkyl group, a, stands for an integer from 1 to 3, and b is the integer 3-a,

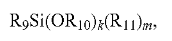

(IV)

wherein $R_9$ stands for a $C_1$-$C_{18}$ alkyl group, $R_{10}$ represents a hydrogen atom or a $C_1$-$C_6$ alkyl group, $R_{11}$ represents a $C_1$-$C_6$ alkyl group k is an integer from 1 to 3, and m stands for the integer 3-k, and applying an agent (b) to the keratinous material, wherein the agent (b) comprises:

(b1) at least one coloring compound comprising at least one effect pigment comprising i) a substrate platelet, ii) a metal oxide layer, comprising a metal oxide and/or a metal oxide hydrate, provided on the surface of the substrate platelet, iii) a metal particle carrier layer provided on the surface of the metal oxide layer, and iv) metal particles provided on the surface of the metal particle carrier layer, and (b2) at least one film-forming polymer.

2. The method according to claim 1, wherein the agent (a) further comprises at least one organic silicon compound of the formula (II)

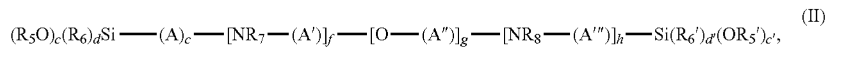

(II)

wherein

R5, R5', R5" independently represent a hydrogen atom or a $C_1$-$C_6$ alkyl group, R6, R6' and R6" independently represent a $C_1$-$C_6$ alkyl group, A, A', A", A'" and A"" independently represent a linear or branched, bivalent $C_1$-$C_{20}$ alkylene group, $R_7$ and $R_8$ independently represent a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III),

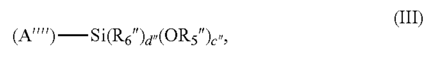

(III)

wherein c, stands for an integer from 1 to 3, d stands for the integer 3-c, c' stands 'for an integer from 1 to 3, d' stands for the integer 3-c', c" stands, for an integer from 1 to 3, d" stands for the integer 3-c", e stands for 0 or 1, f stands for 0 or 1, g stands for 0 or 1, h stands for 0 or 1, provided that at least one of e, f, g and h is different from 0.

3. The method according to claim 1, wherein the agent (a) comprises at least one organic silicon compound of formula (I),

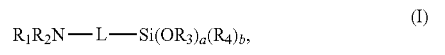

(I)

wherein $R_1$, $R_2$ both represent a hydrogen atom, and

L represents a linear, bivalent $C_1$-$C_6$-alkylene group, $R_3$ represents a hydrogen atom, an ethyl group or a methyl group, $R_4$ represents a methyl group or an ethyl group, a stands for the number 3 and b stands for the number 0.

4. The method according to claim 3, wherein the agent (a) comprises at least one organic silicon compound of formula (I) selected from:

(3-Aminopropyl)triethoxysilane (3-Aminopropyl)trimethoxysilane 1-(3-Aminopropyl)silantriol (2-Aminoethyl)triethoxysilane (2-Aminoethyl)trimethoxysilane 1-(2-Aminoethyl)silantriol (3-Dimethylaminopropyl)triethoxysilane (3-Dimethylaminopropyl)trimethoxysilane 1-(3-Dimethylaminopropyl)silantriol (2-Dimethylaminoethyl)triethoxysilane, (2-Dimethylaminoethyl)trimethoxysilane, 1-(2-Dimethylaminoethyl)silantriol or mixtures thereof.

5. The method according claim 2, wherein the agent (a) comprises at least one organic silicon compound of the formula (II),

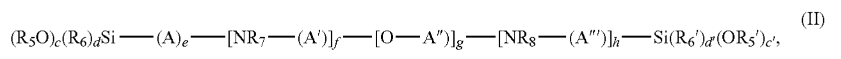

wherein e and f both stand for the number 1, g and h both stand for the number 0, A and A' independently represent a linear, bivalent $C_1$-$C_6$ alkylene and R7 represents a hydrogen atom, a methyl group, a 2-hydroxyethyl group, a 2-alkenyl group, a 2- aminoethyl group or a group of formula (III).

6. The method according to claim 5, wherein the agent (a) comprises at least one organic silicon compound of the formula (II) which is selected from:

3-(Trimethoxysilyl)-N-[3-(trimethoxysilyl) propyl]-1-propanamine 3-(Triethoxysilyl)-N-[3-(triethoxysilyl) propyl]-1-propanamine N-Methyl-3-(trimethoxysilyl)-N-[3-(trimethoxysilyl)propyl]-1-propanamine N-Methyl-3-(triethoxysilyl)-N-[3-(triethoxysilyl)propyl]-1-propane amine 2-[Bis[3-(trimethoxysilyl) propyl]amino]-ethanol 2-[Bis[3-(triethoxysilyl) propyl]amino]-ethanol 3-(Trimethoxysilyl)-N,N-bis[3-(trimethoxysilyl) propyl]-1-propanamine 3-(Triethoxysilyl)-N,N-bis[3-(triethoxysilyl) propyl]-1-propanamine N1,N1-Bis[3-(trimethoxysilyl)propyl]-1,2-ethanediamine, N1,N1-Bis[3-(triethoxysilyl)propyl]-1,2-ethanediamine, N,N-Bis[3-(trimethoxysilyl)propyl]-2-propen-1-amine, N,N-Bis[3-(triethoxysilyl)propyl]-2-propen-1-amine or mixtures thereof.

7. The method according to claim 1, wherein the agent (a) comprises at least one organic silicon compound of formula (IV) selected from:

Methyltrimethoxysilane

Methyltriethoxysilane

Ethyltrimethoxysilane

Ethyltriethoxysilane

Propyltrimethoxysilane

Propyltriethoxysilane

Hexyltrimethoxysilane

Hexyltriethoxysilane

Octyltrimethoxysilane

Octyltriethoxysilane

Dodecyltrimethoxysilane,

Dodecyltriethoxysilane,

Octadecyltrimethoxysilane,

Octadecyltriethoxysilane or mixtures thereof.

8. The method according to claim 1, wherein the substrate platelet comprises aluminum.

9. The method according to claim 1, wherein the metal oxide layer comprises silica.

10. The method according to claim 1, wherein:

the metal particle carrier layer comprises at least one element selected from Sn, Pd, Pt, or Au and/or the metal particles comprise at least one element selected from Cu, Ni or Ag.

11. The method according to claim 1, wherein the composition (a) further comprises at least one coloring compound (a2) selected from colored metal oxides, metal hydroxides, metal oxide hydrates, silicates, metal sulfides, complex metal cyanides, metal sulfates, bronze pigments and/or from colored mica-or mica-based pigments coated with at least one metal oxide and/or a metal oxychloride.

12. A kit-of-parts for dyeing keratinous material, comprising separately packaged:

a first container comprising an agent (a), wherein the agent (a) comprises at least one organic silicon compound of the formula I and at least one organic silicon compound of the formula IV,

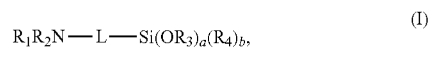

wherein $R_1$, $R_2$ independently represent a hydrogen atom or a $C_1$-$C_6$ alkyl group, L is a linear or branched, bivalent $C_1$-$C_{20}$ alkylene group, $R_3$ is a hydrogen atom or a $C_1$-$C_6$ alkyl group, $R_4$ stands for a $C_1$-$C_6$ alkyl group, a, stands for an integer from 1 to 3, and b is the integer 3-a,

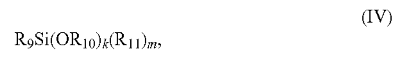

wherein $R_9$ stands for a $C_1$-$C_{18}$ alkyl group, $R_{10}$ represents a hydrogen atom or a $C_1$-$C_6$ alkyl group, $R_{11}$ represents a $C_1$-$C_6$ alkyl group k is an integer from 1 to 3, and m stands for the integer 3-k, and a second container containing an agent (b), wherein the agent contains (b):

(b1) at least one coloring compound comprising at least one effect pigment comprising i) a substrate platelet, ii) a metal oxide layer, comprising a metal oxide and/or a metal oxide hydrate, provided on the surface of the substrate platelet, iii) a metal particle carrier layer provided on the surface of the metal oxide layer, and iv) metal particles provided on the surface of the metal particle carrier layer, and (b2) at least one film-forming polymer.

13. The method of claim 1, wherein:

(a1) is present in a total amount of 5.0 to 10% by weight, based on the total weight of the agent (a); and (b1) is present in an amount of 0.5 to 4.5% by weight, based on the total weight of the agent (b).

14. The method of claim 1, wherein the at least one film-forming polymer comprises a hydrophilic film-forming polymer.

15. The method of claim 1, wherein the keratinous material is human hair.

16. The method of claim 15, wherein the agent (a) has a pH of from 8 to 10.5.

17. The method of claim 16, further comprising:

rinsing the agent (a) from the keratinous material with water before the agent (b) is applied to the keratinous material; and rinsing the agent (b) from the keratinous material with water after the agent (b) is applied to the keratinous material.

18. The method of claim 17, wherein:

the agent (a) is rinsed from the keratinous material 10 seconds to 10 minutes after the agent (a) is applied to the keratinous material; and the agent (b) is rinsed from the keratinous material 10 seconds to 10 minutes after the agent (b) is applied to the keratinous material.

19. A method for dyeing human hair, the method comprising the steps of:

applying an agent (a) to the keratinous material, wherein the agent (a) has a pH of from 8 to 10.5 and comprises:

(a1) at least one organic silicon compound selected from (3-aminopropyl)triethoxysilane or (3-aminopropyl) trimethoxysilane; and additionally at least one organic silicon compound selected from methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane, or octadecyltriethoxysilane; wherein (a1) is present in an amount of from 5.0 to 10% by weight, based on the total weight of the agent (a);

rinsing the agent (a) from the keratinous material with water;

applying an agent (b) to the keratinous material, wherein the agent (b) has a pH of from 8 to 10.5 and comprises:

(b1) at least one coloring compound comprising at least one effect pigment comprising i) a substrate platelet comprising aluminum, ii) a metal oxide layer, comprising silicon dioxide, provided on the surface of the substrate platelet, iii) a metal particle carrier layer, comprising tin oxide, provided on the surface of the metal oxide layer, and iv) silver particles provided on the surface of the metal particle carrier layer; wherein (b1) is present in an amount of 0.5 to 4.5% by weight, based on the total weight of the agent (b); and (b2) at least one hydrophilic film-forming polymer and at least one hydrophobic film-forming polymer; wherein (b2) is present in an amount of from 8 to 12% by weight, based on the total weight of the agent (b); and rinsing the agent (b) from the keratinous material.

* * * * *